(12) United States Patent  
Chuang et al.

(10) Patent No.: US 9,620,547 B2
(45) Date of Patent: Apr. 11, 2017

(54) IMAGE SENSOR, AN INSPECTION SYSTEM AND A METHOD OF INSPECTING AN ARTICLE

(71) Applicant: KLA-Tencor Corporation, Milpitas, CA (US)

(72) Inventors: Yung-Ho Alex Chuang, Cupertino, CA (US); Jingjing Zhang, San Jose, CA (US); John Fielden, Los Altos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 15/201,028

(22) Filed: Jul. 1, 2016

(65) Prior Publication Data

US 2016/0315114 A1 Oct. 27, 2016

Related U.S. Application Data

(63) Continuation of application No. 14/643,148, filed on Mar. 10, 2015, now Pat. No. 9,410,901.

(Continued)

(51) Int. Cl.
*H01L 27/146* (2006.01)
*G01N 21/95* (2006.01)
(Continued)

(52) U.S. Cl.
CPC ... *H01L 27/14632* (2013.01); *G01N 21/8806* (2013.01); *G01N 21/9501* (2013.01);
(Continued)

(58) Field of Classification Search
CPC .......................... H01L 27/1464; H04L 3/11512
See application file for complete search history.

(56) References Cited

U.S. PATENT DOCUMENTS 3,755,704 A 8/1973 Spindt et al.
3,870,917 A 3/1975 Cuny
(Continued)

FOREIGN PATENT DOCUMENTS

EP 0602983 A1 6/1994
EP 0746871 A1 12/1996
(Continued)

OTHER PUBLICATIONS

Pain et al., "A back-illuminated megapixel CMOS image sensor," Jun. 9, 2005, IEEE Workshop on Charge-Coupled Devices and Advanced Image Sensors, Karuizawa, Japan, 4 pages.*
(Continued)

*Primary Examiner* — Kiho Kim
(74) *Attorney, Agent, or Firm* — Bever, Hoffman & Harms, LLP

(57) ABSTRACT

A high sensitivity image sensor comprises an epitaxial layer of silicon that is intrinsic or lightly p doped (such as a doping level less than about $10^{13}$ cm$^{-3}$). CMOS or CCD circuits are fabricated on the front-side of the epitaxial layer. Epitaxial p and n type layers are grown on the backside of the epitaxial layer. A pure boron layer is deposited on the n-type epitaxial layer. Some boron is driven a few nm into the n-type epitaxial layer from the backside during the boron deposition process. An anti-reflection coating may be applied to the pure boron layer. During operation of the sensor a negative bias voltage of several tens to a few hundred volts is applied to the boron layer to accelerate photo-electrons away from the backside surface and create additional electrons by an avalanche effect. Grounded p-wells protect active circuits as needed from the reversed biased epitaxial layer.

14 Claims, 10 Drawing Sheets

Related U.S. Application Data

(60) Provisional application No. 61/954,328, filed on Mar. 17, 2014.

(51) Int. Cl.
*G01N 21/88* (2006.01)
*H01L 27/148* (2006.01)
*H01L 31/107* (2006.01)
*H01L 31/028* (2006.01)
*H01L 31/18* (2006.01)

(52) U.S. Cl.
CPC ...... *H01L 27/1461* (2013.01); *H01L 27/1462* (2013.01); *H01L 27/1464* (2013.01); *H01L 27/14609* (2013.01); *H01L 27/14612* (2013.01); *H01L 27/14643* (2013.01); *H01L 27/14645* (2013.01); *H01L 27/14647* (2013.01); *H01L 27/14685* (2013.01); *H01L 27/14687* (2013.01); *H01L 27/14689* (2013.01); *H01L 27/14698* (2013.01); *H01L 27/14825* (2013.01); *H01L 27/14831* (2013.01); *H01L 27/14856* (2013.01); *H01L 31/028* (2013.01); *H01L 31/107* (2013.01); *H01L 31/1804* (2013.01); *G01N 2201/061* (2013.01); *G01N 2201/0638* (2013.01); *G01N 2201/12* (2013.01); *H01L 27/14681* (2013.01)

(56) References Cited

U.S. PATENT DOCUMENTS

| | | |
|---|---|---|
| 3,947,707 A | 3/1976 | Shannon et al. |
| 4,099,198 A | 7/1978 | Howorth et al. |
| 4,210,922 A | 7/1980 | Shannon |
| 4,275,326 A | 6/1981 | Houtkamp |
| 4,348,690 A | 9/1982 | Jastrzebski et al. |
| 4,467,189 A | 8/1984 | Tsuchiya |
| 4,555,731 A | 11/1985 | Zinchuk |
| 4,644,221 A | 2/1987 | Gutierrez et al. |
| 4,760,031 A | 7/1988 | Janesick |
| 4,853,595 A | 8/1989 | Alfano et al. |
| 5,054,683 A | 10/1991 | Haisma et al. |
| 5,120,949 A | 6/1992 | Tomasetti |
| 5,144,630 A | 9/1992 | Lin |
| 5,227,313 A | 7/1993 | Gluck et al. |
| 5,315,126 A | 5/1994 | Field |
| 5,376,810 A | 12/1994 | Hoenk et al. |
| 5,563,702 A | 10/1996 | Emery et al. |
| 5,717,518 A | 2/1998 | Shafer et al. |
| 5,719,069 A | 2/1998 | Sparks |
| 5,731,584 A | 3/1998 | Beyne et al. |
| 5,742,626 A | 4/1998 | Mead et al. |
| 5,760,809 A | 6/1998 | Malhotra et al. |
| 5,760,899 A | 6/1998 | Eismann |
| 5,852,322 A | 12/1998 | Speckbacher |
| 5,940,685 A | 8/1999 | Loomis et al. |
| 5,999,310 A | 12/1999 | Shafer et al. |
| 6,013,399 A | 1/2000 | Nguyen |
| 6,064,759 A | 5/2000 | Buckley et al. |
| 6,162,707 A | 12/2000 | Dinh et al. |
| 6,201,601 B1 | 3/2001 | Vaez-Iravani et al. |
| 6,271,916 B1 | 8/2001 | Marxer et al. |
| 6,278,119 B1 | 8/2001 | Nikzad et al. |
| 6,285,018 B1 | 9/2001 | Aebi et al. |
| 6,297,879 B1 | 10/2001 | Yang et al. |
| 6,307,586 B1 | 10/2001 | Costello |
| 6,346,700 B1 | 2/2002 | Cunningham et al. |
| 6,362,484 B1 | 3/2002 | Beyne et al. |
| 6,373,869 B1 | 4/2002 | Jacob |
| 6,403,963 B1 | 6/2002 | Nikzad et al. |
| 6,545,281 B1 | 4/2003 | McGregor et al. |
| 6,608,676 B1 | 8/2003 | Zhao et al. |
| 6,711,283 B1 | 3/2004 | Soenksen |
| 6,837,766 B2 | 1/2005 | Costello |
| 7,005,637 B2 | 2/2006 | Costello et al. |
| 7,039,157 B2 | 5/2006 | Fujii et al. |
| 7,126,699 B1 | 10/2006 | Wihl et al. |
| 7,130,039 B2 | 10/2006 | Vaez-Iravani et al. |
| 7,283,166 B1 | 10/2007 | Billman |
| 7,313,155 B1 | 12/2007 | Mu et al. |
| 7,345,825 B2 | 3/2008 | Chuang et al. |
| 7,352,457 B2 | 4/2008 | Kvamme et al. |
| 7,446,474 B2 | 11/2008 | Maldonado et al. |
| 7,465,935 B2 | 12/2008 | Urano et al. |
| 7,525,649 B1 | 4/2009 | Leong et al. |
| 7,528,943 B2 | 5/2009 | Brown et al. |
| 7,586,108 B2 | 9/2009 | Nihtianov et al. |
| 7,609,309 B2 | 10/2009 | Brown et al. |
| 7,741,666 B2 | 6/2010 | Nozaki et al. |
| 7,750,280 B2 | 7/2010 | Hwang et al. |
| 7,791,170 B2 | 9/2010 | Chiang et al. |
| 7,800,040 B2 | 9/2010 | Blacksberg et al. |
| 7,875,948 B2 | 1/2011 | Hynecek et al. |
| 7,928,382 B2 | 4/2011 | Hatakeyama et al. |
| 7,952,633 B2 | 5/2011 | Brown et al. |
| 7,985,658 B2 | 7/2011 | Lei et al. |
| 7,999,342 B2 | 8/2011 | Hsu et al. |
| 8,017,427 B2 | 9/2011 | Manabe |
| 8,138,485 B2 | 3/2012 | Nihtianov et al. |
| 8,309,443 B2 | 11/2012 | Tanaka et al. |
| 8,450,820 B2 | 5/2013 | Nanver et al. |
| 8,455,971 B2 | 6/2013 | Chen et al. |
| 8,513,587 B2 | 8/2013 | Wang et al. |
| 8,514,587 B2 | 8/2013 | Zhang et al. |
| 8,629,384 B1 | 1/2014 | Biellak et al. |
| 8,665,536 B2 | 3/2014 | Armstrong |
| 8,686,331 B2 | 4/2014 | Armstrong |
| 8,755,417 B1 | 6/2014 | Dribinski |
| 8,873,596 B2 | 10/2014 | Dribinski et al. |
| 8,891,079 B2 | 11/2014 | Zhao et al. |
| 8,896,917 B2 | 11/2014 | Armstrong |
| 8,929,406 B2 | 1/2015 | Chuang et al. |
| 8,976,343 B2 | 3/2015 | Genis |
| 2001/0017344 A1 | 8/2001 | Aebi |
| 2002/0191834 A1 | 12/2002 | Fishbaine |
| 2003/0043876 A1 | 3/2003 | Lublin et al. |
| 2003/0222579 A1 | 12/2003 | Habib et al. |
| 2004/0021061 A1 | 2/2004 | Bijkerk |
| 2004/0056279 A1 | 3/2004 | Niigaki et al. |
| 2004/0227070 A1 | 11/2004 | Bateman et al. |
| 2005/0122021 A1 | 6/2005 | Smith et al. |
| 2005/0167575 A1 | 8/2005 | Benz et al. |
| 2005/0190452 A1 | 9/2005 | Govorkov et al. |
| 2005/0233493 A1* | 10/2005 | Augusto ............ G02B 1/005 438/51 |
| 2005/0264148 A1 | 12/2005 | Maldonado et al. |
| 2006/0054778 A1 | 3/2006 | Suhling |
| 2006/0055321 A1 | 3/2006 | Maldonado et al. |
| 2006/0069460 A1 | 3/2006 | Smith et al. |
| 2006/0170324 A1 | 8/2006 | Machuca et al. |
| 2007/0002465 A1 | 1/2007 | Chuang et al. |
| 2007/0034987 A1 | 2/2007 | Costello et al. |
| 2007/0096648 A1 | 5/2007 | Nakajima et al. |
| 2007/0103769 A1 | 5/2007 | Kuwabara |
| 2007/0188744 A1 | 8/2007 | Leslie et al. |
| 2007/0291810 A1 | 12/2007 | Luo et al. |
| 2008/0044932 A1 | 2/2008 | Samoilov et al. |
| 2008/0182092 A1 | 7/2008 | Bondokov et al. |
| 2008/0267241 A1 | 10/2008 | Brown et al. |
| 2008/0315092 A1 | 12/2008 | Kley |
| 2008/0315121 A1 | 12/2008 | Nihtianov et al. |
| 2009/0021717 A1 | 1/2009 | Nihtianov et al. |
| 2009/0091752 A1 | 4/2009 | Terasawa et al. |
| 2009/0108207 A1 | 4/2009 | Liu |
| 2009/0125242 A1 | 5/2009 | Choi et al. |
| 2009/0128912 A1 | 5/2009 | Okada et al. |
| 2009/0168152 A1 | 7/2009 | Gelernt et al. |
| 2009/0180176 A1 | 7/2009 | Armstrong et al. |
| 2010/0102213 A1 | 4/2010 | Garris |
| 2010/0103409 A1 | 4/2010 | Ohshima et al. |
| 2010/0148667 A1 | 6/2010 | Niigaki et al. |
| 2010/0188655 A1 | 7/2010 | Brown et al. |
| 2010/0301437 A1 | 12/2010 | Brown |

(56) References Cited

U.S. PATENT DOCUMENTS

| | | | |
|---|---|---|---|
| 2011/0073982 A1 | 3/2011 | Armstrong et al. |
| 2011/0101219 A1 | 5/2011 | Uchiyama et al. |
| 2011/0116077 A1 | 5/2011 | Chuang et al. |
| 2011/0169116 A1 | 7/2011 | Nanver et al. |
| 2011/0234790 A1 | 9/2011 | True |
| 2011/0256655 A1 | 10/2011 | Nikzad et al. |
| 2011/0261354 A1 | 10/2011 | Sinfield et al. |
| 2011/0291109 A1 | 12/2011 | Wraback et al. |
| 2012/0012811 A1 | 1/2012 | Deflumere et al. |
| 2012/0012957 A1 | 1/2012 | Larsen et al. |
| 2012/0081684 A1 | 4/2012 | Den et al. |
| 2012/0132823 A1 | 5/2012 | Menge et al. |
| 2012/0160993 A1 | 6/2012 | Nevet et al. |
| 2012/0170021 A1 | 7/2012 | Walsh |
| 2012/0228485 A1 | 9/2012 | Iwakiri et al. |
| 2012/0268722 A1 | 10/2012 | Nihtianov et al. |
| 2013/0009069 A1 | 1/2013 | Okada |
| 2013/0016346 A1 | 1/2013 | Romanovsky et al. |
| 2013/0017205 A1 | 1/2013 | Giaccia et al. |
| 2013/0020491 A1 | 1/2013 | Mazzillo |
| 2013/0056843 A1 | 3/2013 | Lee et al. |
| 2013/0077086 A1 | 3/2013 | Chuang et al. |
| 2013/0082241 A1 | 4/2013 | Kub et al. |
| 2013/0088706 A1 | 4/2013 | Chuang et al. |
| 2013/0126705 A1 | 5/2013 | Maleev |
| 2013/0148112 A1 | 6/2013 | Chuang et al. |
| 2013/0169957 A1 | 7/2013 | Wolf et al. |
| 2013/0176552 A1 | 7/2013 | Brown et al. |
| 2013/0194445 A1 | 8/2013 | Brown et al. |
| 2013/0264481 A1 | 10/2013 | Chern et al. |
| 2013/0270663 A1 | 10/2013 | Lin et al. |
| 2013/0313440 A1 | 11/2013 | Chuang et al. |
| 2013/0320211 A1 | 12/2013 | Park et al. |
| 2013/0336574 A1 | 12/2013 | Nasser-Ghodsi et al. |
| 2014/0034816 A1 | 2/2014 | Chuang et al. |
| 2014/0111799 A1 | 4/2014 | Lei et al. |
| 2014/0158864 A1 | 6/2014 | Brown et al. |
| 2014/0203386 A1 | 7/2014 | Bui |
| 2014/0204963 A1 | 7/2014 | Chuang et al. |
| 2014/0226140 A1 | 8/2014 | Chuang et al. |
| 2014/0246595 A1 | 9/2014 | Menge et al. |
| 2014/0291493 A1 | 10/2014 | Chuang et al. |
| 2014/0305367 A1 | 10/2014 | Chuang et al. |
| 2014/0362203 A1 | 12/2014 | Delaney et al. |
| 2015/0007765 A1 | 1/2015 | Dribinski |
| 2015/0177159 A1 | 6/2015 | Brown et al. |
| 2015/0200216 A1 | 7/2015 | Muramatsu et al. |
| 2015/0268176 A1 | 9/2015 | Deng et al. |
| 2015/0275393 A1 | 10/2015 | Bondokov et al. |
| 2015/0294998 A1 | 10/2015 | Nihtianov et al. |
| 2016/0056606 A1 | 2/2016 | Chuang et al. |

FOREIGN PATENT DOCUMENTS

| | | |
|---|---|---|
| EP | 1939917 A2 | 7/2008 |
| EP | 2346094 A1 | 7/2011 |
| JP | H0511287 A | 1/1993 |
| JP | H10171965 A | 6/1998 |
| JP | 2003043533 A | 2/2003 |
| JP | 2004031452 A | 1/2004 |
| JP | 2007086108 A | 4/2007 |
| JP | 2007249092 A | 9/2007 |
| JP | 2007298932 A | 11/2007 |
| JP | 2009117454 A | 5/2009 |
| KR | 100688497 B1 | 3/2007 |
| KR | 100826407 B1 | 5/2008 |
| RU | 2297070 C2 | 4/2007 |
| WO | 9532518 A1 | 11/1995 |
| WO | 9617372 A1 | 6/1996 |
| WO | 2007035858 A2 | 3/2007 |
| WO | 2011091159 A1 | 7/2011 |
| WO | 2014067754 A2 | 5/2014 |

OTHER PUBLICATIONS

U.S. Appl. No. 61/720,700—Certified Copy corres to PCT/EP2013/071080, pp. 1-44.

Allen et al., Work Function, Photoelectric Threshold, and Surface . . . ; Physical Review, vol. 127, No. 1, Jul. 1, 1962, pp. 150-158.

Armstrong, Carter M.The Quest for the Ultimate Vacuum Tube, Spectrum IEEE, Dec. 2015, 4 pgs.

Ding, MengField Emission from Silicon, MIT 2001, 277 pgs.

Dulinski et al., Tests of a backside illuminated monolithic CMOS pixel . . . , Nuclear Instruments and Methods in Physics Research A 546 (2005) 274-280, 7 pgs.

Field Emitter Review, 7 pgs in Japanese.

Fowler, R. H., et al, Electron Emission in Intense Electric Fields, Mar. 31, 1928, 9 pgs.

Fu et al., Optimizing GaN photocathode structure for higher . . . ; Optik, vol. 123, No. 9, May 2012, pp. 756-768.

Grubisic et al., New Silicon Reach-Through Avalanche Photodiodes with Enhanced Sensitivity in the DUV/UV Wavelength Range, MIPRO 2013, May 20-24, 2013, pp. 48-54.

Hecht, Optics, Fourth Edition, India: Pearson Education Pte, Ltd. 2004.

Hecht, Optics, Second Edition, Adelphi University, 1987, Addison-Wesley Publishing Company, Inc., 3 pages.

Henderson, Brian S., Study of Negative Electron Affinity . . . , Dept. of Physics, Rice Univ., Aug. 7, 2009, 18 pgs.

Herriott et al., Folded Optical Delay Lines, Applied Optics 4, #8, pp. 883-889 (1965).

Herriott et al., Off-Axis Paths in Spherical Miccor Interferometers, Applied Optics 3, #4, pp. 523-526 (1964).

Howarth et al., Transmission silicon photoemitters . . . , Jrnl of Physics D: Applied Physics, vol. 9, No. 5, Apr. 1, 1976, pp. 785-794.

Huang et al., Back-Side Illuminated Photogate CMOS . . . , IEEE Sensors Journal, vol. 11, No. 9, Sep. 2011, 5 pgs.

Itzler et al., InP-based Geiger-mode . . . , Proc. SPIE vol. 7320 (2000), 12 pgs.

KLA-TENCOR Coporation, filed application U.S. Appl. No. 62/059,368, filed Oct. 3, 2014 and entitled "183nm Laser and Inspection System".

Koike, AkifumiField Emitter Equipped With a Suppressor to Control Emission Angel, IEEE Electron Device Letters, vol. 34, No. 5, May 2013, 3 pgs.

Martinelli, Ramon U., Infrared Photoemission from Silicon, Applied Physics Letters, vol. 16, No. 7, Apr. 1, 1970, pp. 261-262.

Martinelli, Ramon U., Reflection and Transmission Secondary Emission . . . , Applied Physics Letters, vol. 17, No. 8, Oct. 15, 1970, pp. 313-314.

Nagao, Masayoshi, Cathode Technologies for Field Emission Displays, IEEJ Trans 2006; 1:171-178, 8 pgs.

Nagao, MasayoshiFabrication of a Field Emitter Array with a Built-In Einzel Lens, JJAP 48 (2008) 06FK02, 4 pgs.

Nanver et al., Pure-Boron Chemical-Vapor-Deposited Layers: a New Material for Silicon Device Processing, 18th IEEE International Conference on Advanced Thermal Processing of Semiconductors (RTP), Sep. 28, 2010-Oct. 1, 2010, pp. 136-139.

Nanver, Silicon Photodiodes for Low Penetration Depth Beams such as DUV/VUV/EUV Light and Low-Energy Electrons, Advances in Photodiodes, G. Betta, ed., Mar. 22, 2011, pp. 205-224, www.intechopen.com.

Neo, YoichiroElectron Optical Properties of Microcolumn with Field Emitter, JJAP 52 (2013) 036603, 5 pgs.

Niclass et al., Design and Characterization of a CMOS 3-D . . . , IEEE Journal Solid-State Circuits, vol. 40, No. 9, Sep. 2005, 8 pgs.

Nikzad, Shouleh et al., Delta-doped CCDs High QE with long-term stability . . . ; SPIE vol. 2198 (1994) pp. 907-915.

Omatsu et al., High repetition rate Q-switching performance . . . , Optics Express vol. 14, Issue 7, pp. 2727-2734, Apr. 3, 2006.

Paetzel et al., Activation of Silicon Wafer by Excimer Laser, 18th IEEE Conf. Advanced Thermal Processing of Semiconductors—RTP 2010, 5 pgs.

(56) References Cited

OTHER PUBLICATIONS

Rakhshandehroo, M.R. et al, Fabrication of a self-aligned silicon field emission . . . , JVSTB, 16, 765 (1998); doi: 10.1116/1,589900, 6 pgs.

Rakhshandehroo, M.R. et al, Field emission from gated Si emitter tips with precise . . . , JVSTB, 15, 2777 (1997); doi: 10.1116/1.589726, 6 pgs.

Raoult, Efficient generation of narrow-bandwidth . . . , Jul. 15, 1998, vol. 23, No. 14, Optics Letters, pp. 1117-1119.

Sakic, Agata, Boron-layer silicon photodiodes for high-efficiency low-energy electron detection, Solid-State Electronics 65-66 (2011), pp. 38-44.

Sarubbi et al., Chemical Vapor Deposition of α-Boron Layers on Silicon for Controlled Nanometer-Deep p+ n Junction Formation, J. Electron. Mat., vol. 39, No. 2, Feb. 2010, pp. 162-173.

Sarubbi et al., Pure boron-doped photodiodes . . . IEEE, Sep. 15, 2008, pp. 278-281.

Sato, T., et al, Fabrication and characterization of HfC coated . . . , J. Vac. Sci. Technol. B 2194), published Jul. 31, 2003, 5 pgs.

Serbun Pavel et al, Stable field emission of single B-doped . . . , JVSTB, 31, 02B101 (2013); doi: 10.1116/1.4765088, 7 pgs.

Sobieski, Stanley, Intensified Charge Coupled Devices for Ultra Low Light Level Imaging, NASA, Goddard Space Flight Center, SPIE vol. 78 (1976) Low Light Level Devices, pp. 73-77.

Stevanovic et al., A CMOS Image Sensor for High-Speed Imaging, 2000 IEEE int'l. Solid-State Circuits Conf., 3 pgs.

Tobin, Kenneth W., Inspection in Semiconductor Manufacturing, Webster's Encyclopedia of Electrical and Electronic Engineering, vol. 10, pp. 242-262, Wiley & Sons, NY, NY, 1999.

Utsumi, TakaoVacuum Microelectrnoics: What's New and Exciting, IEEE vol. 38, No. 10, Oct. 1991, 8 pgs.

Xiaogian, Fu, Higher Quantum Efficiency by Optimizing . . . 978-1-4244-6644-3/10 IEEE, pp. 234-235.

* cited by examiner

IMAGE SENSOR, AN INSPECTION SYSTEM AND A METHOD OF INSPECTING AN ARTICLE

RELATED APPLICATIONS

The present application is a continuation of U.S. patent application Ser. No. 14/643,148, entitled "AN IMAGE SENSOR, AN INSPECTION SYSTEM AND A METHOD OF INSPECTING AN ARTICLE" by Chuang et al. and filed on Mar. 10, 2015, which claims priority to U.S. Provisional Patent Application 61/954,328, entitled "AN IMAGE SENSOR, AN INSPECTION SYSTEM AND A METHOD OF INSPECTING AN ARTICLE", filed on Mar. 17, 2014, and incorporated by reference herein.

The present application is related to U.S. patent application Ser. No. 14/273,424 entitled "Low-Noise Sensor And An Inspection System Using A Low-Noise Sensor" and filed by Brown et al. on May 8, 2014, to U.S. patent application Ser. No. 11/805,907 entitled "Inspection System Using Back Side Illuminated Linear Sensor" and filed by Armstrong et al. on May 25, 2007, to U.S. patent application Ser. No. 13/364,308 entitled "High-density digitizer" and filed by Brown et al. on Feb. 1, 2012, to U.S. patent application Ser. No. 14/096,911 entitled "Method and apparatus for high-speed acquisition of moving images using pulsed illumination" and filed by Brown et al. on Dec. 4, 2013, to U.S. patent application Ser. No. 13/622,155 entitled "Interposer Based Imaging Sensor for High-Speed Image Acquisition and Inspection Systems" and filed by Brown et al. on Sep. 18, 2012, and to U.S. patent application Ser. No. 13/792,166 entitled "Back-Illuminated Sensor With Boron Layer" and filed by Chern et al. on Mar. 10, 2013. It is also related to U.S. Pat. No. 7,609,309 entitled "Continuous Clocking of TDI Sensors" to Brown et al., U.S. Pat. No. 7,952,633 entitled "Apparatus for Continuous Clocking of TDI Sensors" to Brown et al., and U.S. Pat. No. 8,624,971 "TDI Sensor Modules with Localized Driving and Signal Processing Circuitry for High Speed Inspection" to Brown et al. All of these patents and applications are incorporated by reference herein.

BACKGROUND OF THE DISCLOSURE

Field of the Disclosure

The present application relates to images sensors suitable for detecting images at vacuum UV (VUV), deep UV (DUV), visible and near infra-red (NIR) wavelengths, and to inspection systems incorporating such sensors. In particular it relates to sensors and methods for fabricating sensors with low noise and high sensitivity. The sensors are particularly suitable for use in inspection systems including those used to inspect photomasks, reticles, and semiconductor wafers.

Related Art

The integrated circuit industry requires inspection tools with increasingly higher sensitivity to detect ever smaller defects and particles including those with dimensions close to 10 nm or smaller. Furthermore these inspection tools must operate at high speed in order to inspect 100%, or a large fraction, of the area of a photomask, reticle or wafer, usually in less than one hour. Some applications require many (such as about 50 or 100) wafers to be inspected in one hour. Generally short wavelengths such as UV, deep UV (DUV) and vacuum UV (VUV) wavelengths have higher sensitivity for detecting small defects and particles compared with longer wavelengths. Inspection of photomasks or reticles is best done using the same wavelength as used for lithography, which is currently a wavelength of substantially 193.4 nm for the most critical lithography steps and substantially 248 nm for less critical steps. High-speed inspection requires sensors with high sensitivity and low noise in order to detect the small amount of light scattered from small particles or defects or allow detection of small changes in reflectivity due to defects in the pattern. An image sensor that can detect a change in light level of one, or a few, photons is highly desirable.

Silicon CMOS and CCD image sensors are known in the art. CCD image sensors are particularly suitable for high-speed inspection systems for semiconductor wafers, photomasks and reticles because the electronic noise of such sensors is quite low and follows closely a Poisson statistical distribution (apart from very infrequent events caused by absorption of charged particles from cosmic rays or radio-active decay, which are rare and can generally be filtered out by image processing software). Silicon CCD image sensors can have noise levels equivalent to about 2 electrons RMS if the sensor is cooled to about 100° K and is read out at a relatively low speed (such as a rate of a few hundred thousand pixels per second or less) and appropriate driving and reading electronics are used. Such sensors, when operated at similar speeds, but at a temperature closer to room temperature (such as about −10° C.) may have noise levels equivalent to about 5-10 electrons RMS. However high-speed inspection systems require data rates of multiple billions of pixels per second, which are generally achieved by reading many tens or a few hundred pixels (taps) simultaneously at rates of several to a few tens of millions of pixels per second. Such high data rates and so many output channels operating at the same time generate many Watts of heat making cooling below room temperature impractical. The high speed operation itself also generates more electrical noise and, when combined with the high operating temperature, can lead to noise levels equivalent to about 20 to 40 electrons RMS.

CMOS sensors typically have higher noise levels than CCD sensors because CMOS transistors have their channels on the surface of the silicon resulting in noise from the silicon to silicon dioxide interface (due to defects and traps at that interface). Furthermore this noise from the surface defects and traps does not closely follow Poisson statistics. Even if the RMS noise is low, high noise spikes are much more frequent than would be expected from Poisson statistics. This is a serious problem for inspection systems, as these high noise spikes can result in a false detection of a defect. Systems with a CMOS detector may have high rates of reporting false defect rates when operated in their highest sensitivity modes. A reinspection would be needed to separate false from true defects, slowing down the inspection.

For UV wavelengths, when a photon is absorbed in silicon, usually only a single electron-hole pair is created, but occasionally two pairs may be created, resulting in average yield per absorbed photon slightly greater than 1. At DUV and VUV wavelengths, the probability of a second electron-hole pair being produced increases so the average electron yield increases. For example, when photons of a vacuum wavelength of 193 nm are absorbed in silicon, the average yield is about 1.7 electron-hole pairs per absorbed photon. For wavelengths currently used in semiconductor inspection systems and wavelengths likely to be used within the next several years, the electron-hole pair yield will not exceed 2. Hence silicon CCD and CMOS sensors are not able to reliably detect one, or a few, photons when sensing visible, UV, DUV or VUV wavelengths.

Avalanche photodiodes are known in the art. An avalanche photodiode uses a relatively large reverse bias voltage (tens to a few hundred volts) over a distance of about one hundred or a few hundred microns of silicon in order to generate multiple carriers (electrons or holes) from a single carrier created by photon absorption. When a photon is absorbed, an electron-hole pair is created, usually close to the surface when sensing UV radiation because of the strong absorption of silicon at UV wavelengths. The bias voltage accelerates the carriers. When a carrier has accelerated to a high enough speed to have about 3.7 eV of energy, it can create an additional electron-hole pair by collision. This process can be repeated a few times creating more carriers and, hence, a large signal.

Most common avalanche diodes absorb the incident light in n-type silicon and apply a bias voltage to accelerate holes away from the surface. This is because surface defects on the silicon tend to have positive charges and attract electrons. Furthermore, to make an avalanche detector that uses electrons rather than holes requires doping the light absorbing silicon to p-type silicon. Boron is the only practically useful p-type dopant for silicon. Boron diffuses easily into silicon dioxide create positive charges in the oxide. This further increases the electron recombination rate at the surface and makes conventional electron-based avalanche photodiodes less efficient for UV, DUV and VUV wavelengths. The avalanche gain and mobility are both lower for holes than electrons in silicon. So avalanche diodes using holes need a longer length in silicon and/or a higher operating voltage in order to achieve a given gain factor.

Therefore, a need arises for a sensor overcoming some, or all, of the above disadvantages. In particular a need arises for an image sensor that can detect very low levels of UV, DUV and/or VUV light while operating at very high data rates, such as billions of pixels per second.

SUMMARY OF THE DISCLOSURE

An exemplary inspection system is described. This inspection system includes an illumination source, optics, and a detector. The illumination source includes a UV, DUV or VUV laser that generates light at one, or a few, discrete wavelengths, or the illumination source includes laser-sustained plasma light source that emits broadband light including light at UV, DUV and/or VUV wavelengths. The optics are configured to direct and focus radiation from the illumination source onto a sample. The sample is supported by a stage, which moves relative to the optics during the inspection. The detector is configured to receive reflected or scattered light from the sample, wherein the optics are further configured to collect, direct, and focus the reflected or scattered light onto the detector. The detector includes one or more backside-illuminated avalanche image or line sensors as described below. In one embodiment, at least one image sensor is a backside-illuminated avalanche time delay integration (TDI) sensor.

The exemplary inspection system may include one or more illumination paths that illuminate the sample from different angles of incidence and/or different azimuth angles and/or with different wavelengths and/or polarization states. The exemplary inspection system may include one or more collection paths that collect light reflected or scattered by the sample in different directions and/or are sensitive to different wavelengths and/or to different polarization states. The exemplary inspection system may include a backside-illuminated avalanche TDI sensor with readout circuits on two sides that are used to read out two different signals simultaneously.

An exemplary method of inspecting a sample is described. The exemplary method includes directing and focusing radiation from an illumination source onto the sample. The sample is supported by a stage, which moves relative to the optics during the inspection. The method further includes using optics to collect, direct, and focus light reflected or scattered by the sample onto a detector. The detector includes one or more backside-illuminated avalanche image or line sensors. At least one image sensor may be a backside-illuminated avalanche TDI sensor.

Exemplary backside-illuminated avalanche image and line sensors are described. The exemplary image and line sensors may be fabricated with CMOS or CCD technology. The exemplary image and line sensors use electrons to detect near-IR, visible, UV, DUV and/or VUV light with high quantum efficiency. The exemplary image and line sensors incorporate a pure boron layer on their backside (illuminated) surface. The pure boron layer prevents growth of a native oxide on that surface. Furthermore some of the boron diffuses a short distance into the silicon to create a highly doped p-type semiconductor layer just beneath the surface. This p-type layer, in combination with the applied backside negative bias voltage drives electrons away from the surface and minimizes recombination of photo-electrons at or near the surface.

An exemplary method for fabricating backside-illuminated avalanche image and line sensors is described. This method includes fabricating front-side CMOS or CCD circuits and pixels in an intrinsic or lightly p-type doped (such as about $10^{11}$ to $2 \times 10^{13}$ dopant atoms per cubic centimeter (cm³)) epitaxial layer of silicon on a silicon wafer. After the front-side circuits are at least partially fabricated, the wafer is polished or etched to expose, at least, the light sensitive (backside) area. This method further includes depositing a thin (such as 2 nm to 6 nm thick) pure boron layer on the backside surface of the epitaxial silicon layer. In some embodiments, during the boron deposition, the wafer is kept at an elevated temperature (such as 700° C. to 950° C.) for a few minutes, or a few tens of minutes, to drive in some of the boron as a dopant of the silicon.

DETAILED DESCRIPTION OF THE DRAWINGS

The present invention relates to an improvement in sensors for semiconductor inspection systems. The following description is presented to enable one of ordinary skill in the art to make and use the invention as provided in the context of a particular application and its requirements. As used herein, directional terms such as "top", "bottom", "over", "under", "upper", "upward", "lower", "down", "downward", "front-side" and "backside" are intended to provide relative positions for purposes of description, and are not intended to designate an absolute frame of reference. As used herein, the terms image sensor and line sensor are interchangeable except where the description is of a sensor explicitly comprising a 2D array of pixels (generally called an image sensor) or where the description is of a sensor explicitly consisting of a 1D line of pixels (generally called a line sensor). Various modifications to the preferred embodiment will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed.

Figure 1:
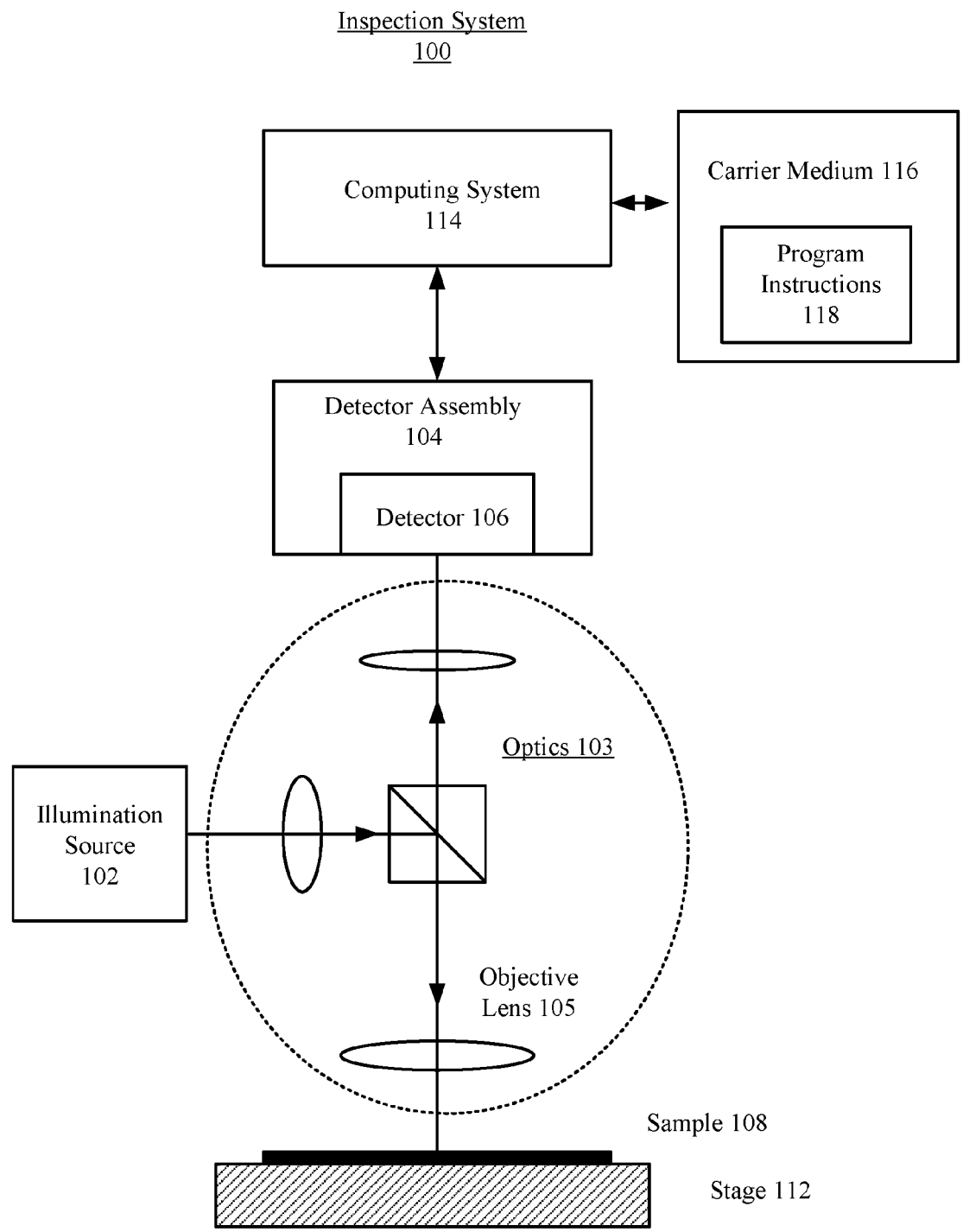
FIG. 1 illustrates an exemplary inspection system incorporating a detector that comprises a backside-illuminated avalanche image or line sensor.

FIG. 1 illustrates an exemplary inspection system 100 configured to measure a sample 108 such as a wafer, reticle, or photomask. Sample 108 is placed on a stage 112 in order to facilitate movement to different regions of sample 108 underneath the optics. Stage 112 may comprise an X-Y stage or an R-θ stage. In some embodiments, stage 112 can adjust the height of sample 108 during inspection to maintain focus. In other embodiments, an objective lens 105 can be adjusted to maintain focus.

An illumination source 102 may comprise one or more lasers and/or a broad-band light source. Illumination source 102 may emit DUV and/or VUV radiation. Optics 103 including an objective lens 105 directs that radiation towards, and focuses it on, sample 108. Optics 103 may also comprise mirrors, lenses, and/or beam splitters. Light reflected or scattered from sample 108 is collected, directed, and focused by optics 103 onto a detector 106, which is within a detector assembly 104.

Detector assembly 104 includes a detector 106. Detector 106 comprises a backside-illuminated avalanche image or line sensor as described herein. Detector 106 may include a two-dimensional image sensor or a one-dimensional line sensor. In one embodiment, the output of detector 106 is provided to a computing system 114, which analyzes the output. Computing system 114 is configured by program instructions 118, which can be stored on a carrier medium 116.

One embodiment of inspection system 100 illuminates a line on sample 108, and collects scattered and/or reflected light in one or more dark-field and/or bright-field collection channels. In this embodiment, the detector 106 may include a backside-illuminated avalanche line sensor.

Another embodiment of inspection system 100 illuminates multiple spots on sample 108, and collects scattered and/or reflected light in one or more dark-field and/or bright-field collection channels. In this embodiment, the detector 106 may include a two-dimensional backside-illuminated avalanche image sensor, or it may comprise multiple discrete backside illuminated avalanche sensors.

Additional details of various embodiments of inspection system 100 can be found in U.S. patent application Ser. No. 13/554,954, entitled "WAFER INSPECTION SYSTEM", filed on Jul. 9, 2012 by Romanovsky et al., U.S. Published Patent Application 2009/0180176, by Armstrong et al., which published on Jul. 16, 2009, U.S. Published Patent Application 2007/0002465 by Chuang et al., which published on Jan. 4, 2007, U.S. Pat. No. 5,999,310, by Shafer et al., which issued on Dec. 7, 1999, and U.S. Pat. No. 7,525,649 by Leong et al., which issued on Apr. 28, 2009. All of these patents and patent applications are incorporated by reference herein.

Figure 2A:
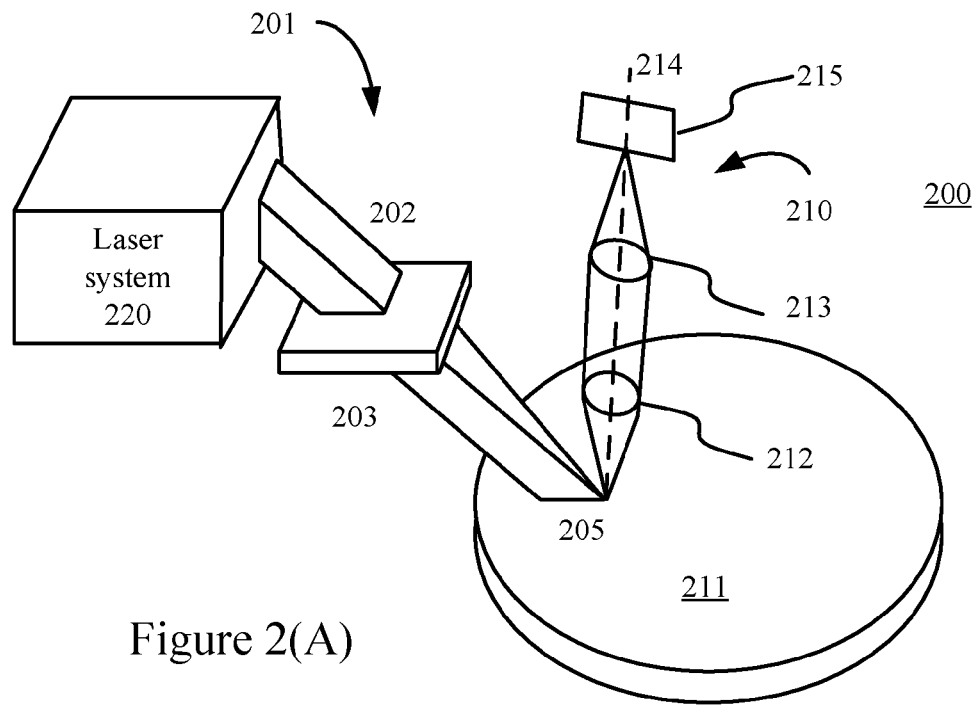
FIGS. 2A and 2B illustrate an exemplary inspection system using line illumination with one, or more, collection channels and one, or more, backside-illuminated avalanche line sensors.
Figure 2B:
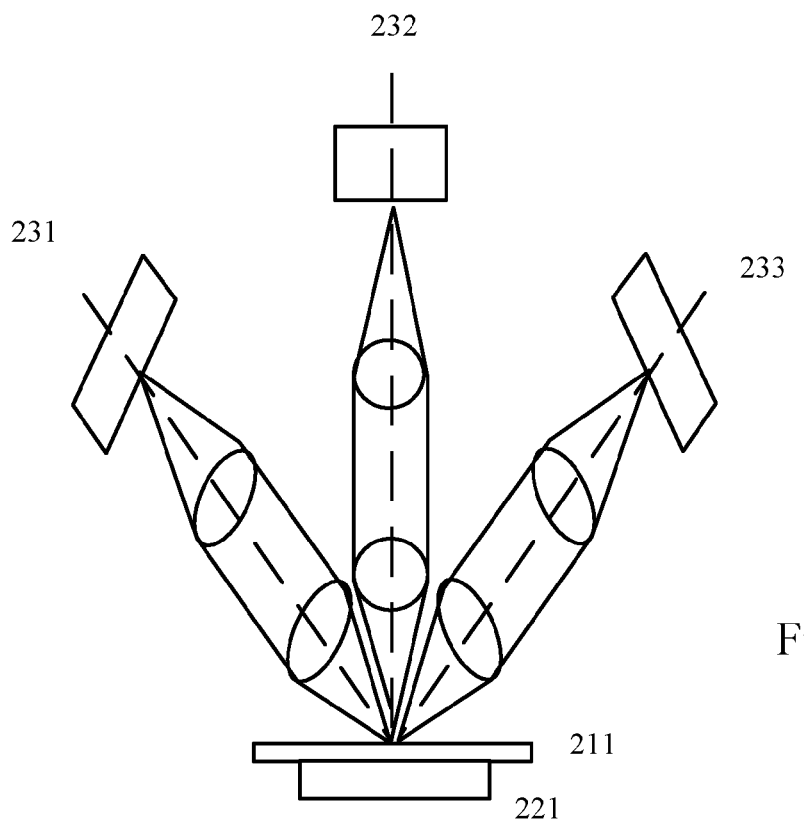

FIGS. 2(A) and 2(B) illustrate aspects of dark-field inspection systems that incorporate the sensors and/or methods described herein in accordance with other exemplary embodiments of the present invention. In FIG. 2(A), illumination optics 201 comprises a DUV or VUV laser system 220 generating light 202 that is focused by mirror or lens 203 into a line 205 on the surface of the wafer or photomask (sample) 211 being inspected. Collection optics 210 directs light scattered from line 205 to sensor 215 using lenses and/or mirrors such as 212 and 213. The optical axis 214 of the collection optics is not in the illumination plane of line 205. In some embodiments, axis 214 is approximately perpendicular to the line 205. Sensor 215 comprises a back-illuminated avalanche array sensor, such as a back-illuminated avalanche line sensor as described herein.

FIG. 2(B) illustrates one embodiment of multiple dark-field collection systems (231, 232 and 233, respectively) each substantially similar to the collection optics 210 of FIG. 2(A). Collection systems 231, 232 and 233 are used in combination with illumination optics substantially similar to illumination optics 201 in FIG. 2(A). One of more of the dark-field collection systems include a back-illuminated avalanche image or line sensor. Sample 211 is supported on stage 221, which moves the areas to be inspected underneath the optics. Stage 221 may comprise an X-Y stage or an R-θ stage, which preferably moves substantially continuously during the inspection in order to inspect large areas of the sample with minimal dead time.

More details of inspection systems in accordance with the embodiments illustrated in FIGS. 2(A) and 2(B) can be found in U.S. Pat. No. 7,525,649. U.S. Pat. No. 6,608,676, which is incorporated by reference herein, also describes line illumination systems suitable for inspection of unpatterned or patterned wafers.

Figure 3:
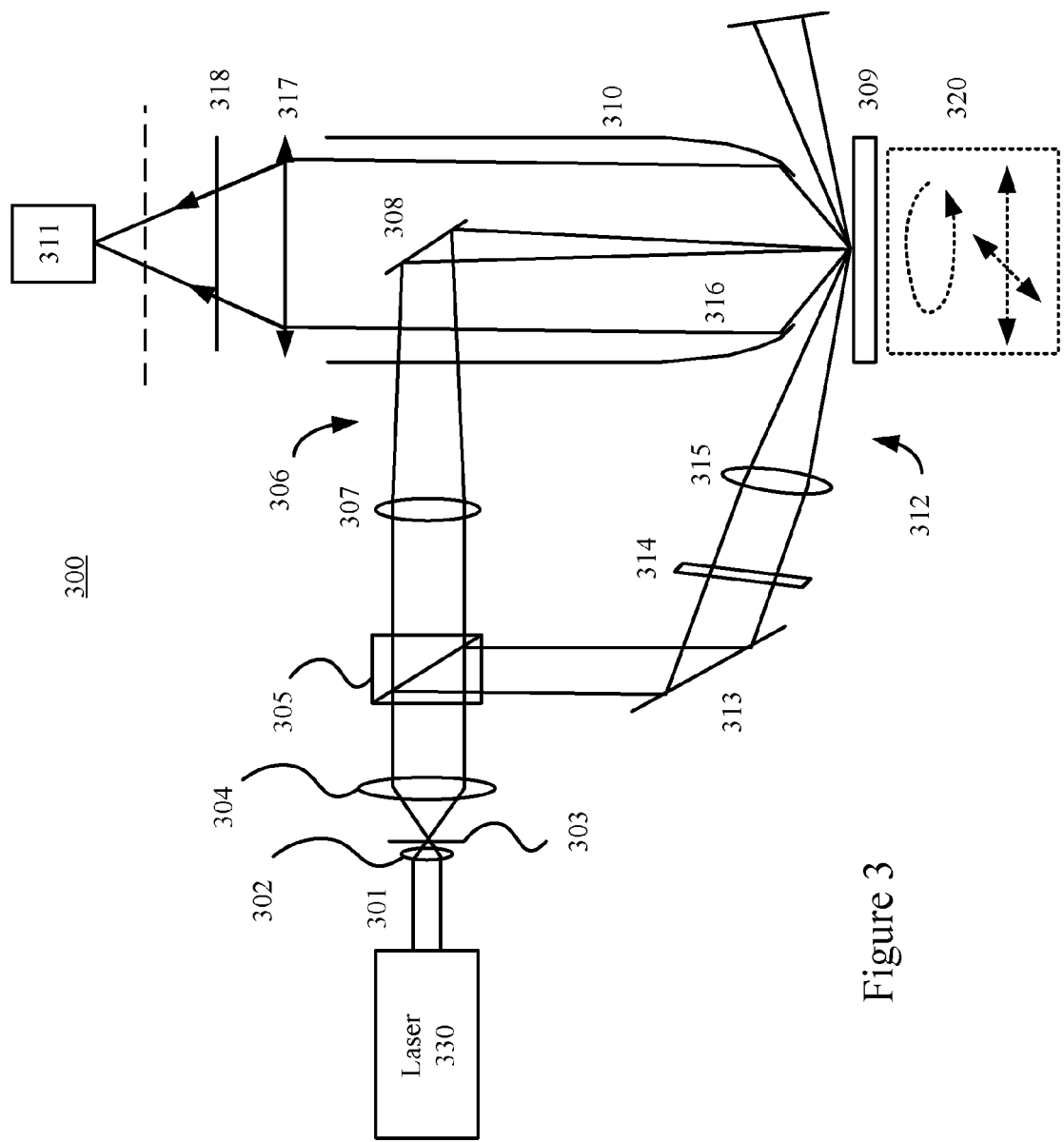
FIG. 3 illustrates an exemplary inspection system with normal and oblique illumination and a backside-illuminated avalanche image or line sensor.

FIG. 3 illustrates an inspection system 300 configured to detect particles or defects on a sample using both normal and oblique illumination beams. In this configuration, a DUV or VUV laser system 330 provides a laser beam 301. A lens 302 focuses the beam 301 through a spatial filter 303. Lens 304 collimates the beam and conveys it to a polarizing beam splitter 305. Beam splitter 305 passes a first polarized component to the normal illumination channel and a second polarized component to the oblique illumination channel, where the first and second components are orthogonal. In the normal illumination channel 306, the first polarized component is focused by optics 307 and reflected by mirror 308 towards a surface of a sample 309. The radiation scattered by sample 309 (such as a wafer or photomask) is collected and focused by a paraboloidal mirror 310 to backside illuminated avalanche sensor 311.

In the oblique illumination channel 312, the second polarized component is reflected by beam splitter 305 to a mirror 313 which reflects such beam through a half-wave plate 314 and focused by optics 315 to sample 309. Radiation originating from the oblique illumination beam in the oblique channel 312 and scattered by sample 309 is collected by paraboloidal mirror 310 and focused to backside-illuminated avalanche sensor 311. The sensor and the illuminated area (from the normal and oblique illumination channels on surface 309) are preferably at the foci of the paraboloidal mirror 310.

The paraboloidal mirror 310 collimates the scattered radiation from sample 309 into a collimated beam 316. Collimated beam 316 is then focused by an objective 317 and through an analyzer 318 to the sensor 311. Note that curved mirrored surfaces having shapes other than paraboloidal shapes may also be used. An instrument 320 can provide relative motion between the beams and sample 309 so that spots are scanned across the surface of sample 309. U.S. Pat. No. 6,201,601, which issued on Mar. 13, 2001 and is incorporated by reference herein, describes inspection system 300 in further detail.

Figure 4:
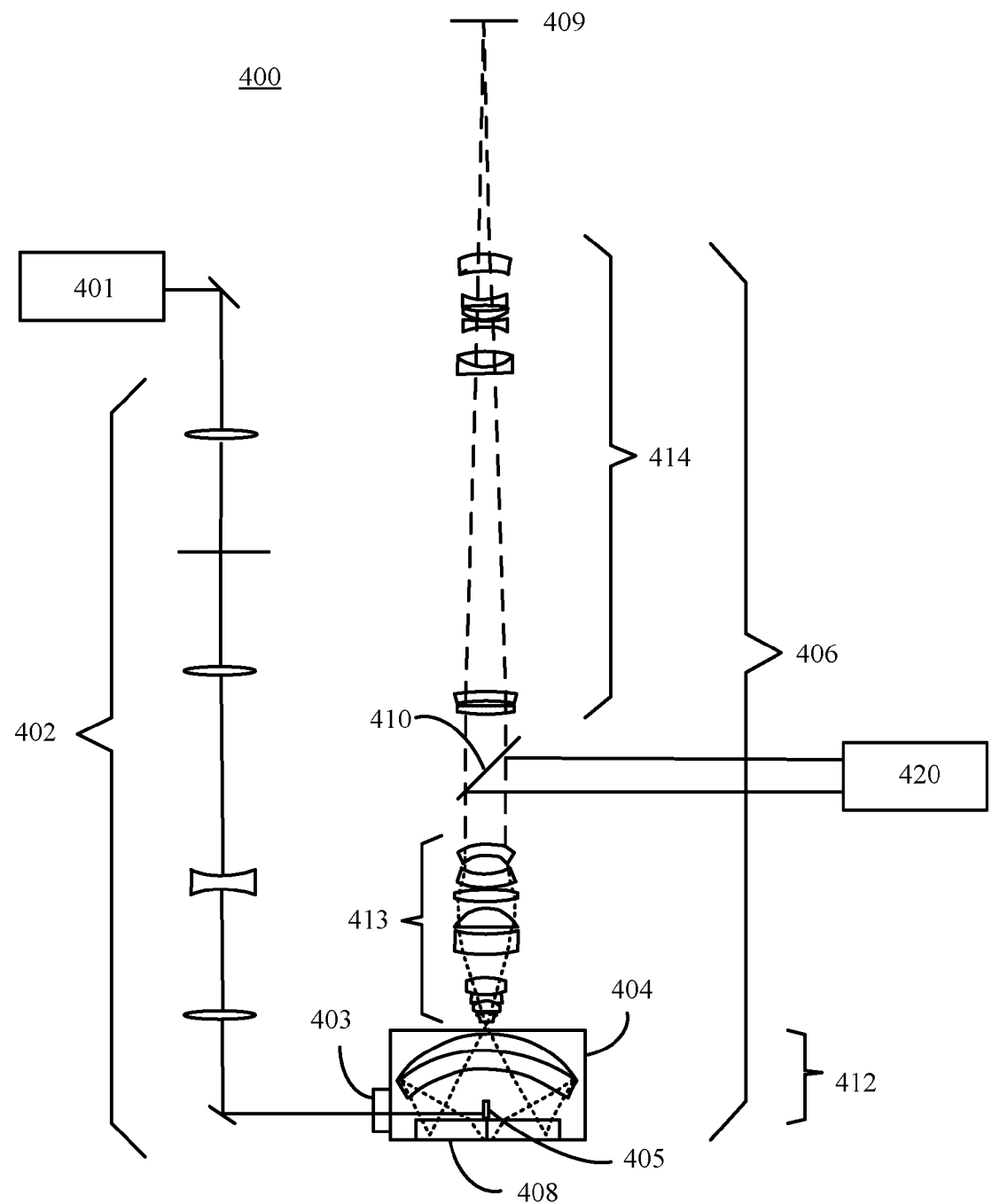
FIG. 4 illustrates an exemplary inspection system with bright-field and dark-field illumination channels and a backside-illuminated avalanche image sensor.

FIG. 4 illustrates an exemplary catadioptric imaging system 400 configured as an inspection system with bright-field and dark-field inspection modes. System 400 may incorporate two illuminations sources: a laser 401, and a broad-band light illumination module 420.

In a dark-field mode, adaptation optics 402 control the laser illumination beam size and profile on the surface being inspected. Mechanical housing 404 includes an aperture and window 403, and a prism 405 to redirect the laser along the optical axis at normal incidence to the surface of a sample 408. Prism 405 also directs the specular reflection from surface features of sample 408 out of objective 406. Objective 406 collects light scattered by sample 408 and focuses it on sensor 409. Lenses for objective 406 can be provided in the general form of a catadioptric objective 412, a focusing lens group 413, and a tube lens section 414, which may, optionally, include a zoom capability.

In a bright-field mode, broad-band illumination module 420 directs broad-band light to beam splitter 410, which reflects that light towards focusing lens group 413 and catadioptric objective 412. Catadioptric objective 412 illuminates the sample 408 with the broadband light. Light that is reflected or scattered from the sample is collected by objective 406 and focused on sensor 409. Broad-band illumination module 420 comprises, for example, a laser-sustained plasma light source or an arc lamp. Broad-band illumination module 420 may also include an auto-focus system to provide a signal to control the height of sample 408 relative to catadioptric objective 412.

Sensor 409 includes a backside-illuminated avalanche image sensor as described herein. In one embodiment, sensor 409 comprises a backside illuminated avalanche image sensor, which is used for dark-field imaging, and a backside illuminated image sensor, which is used for bright-field imaging. Both image sensors may operate in a TDI mode.

Published Patent Application 2007/0002465, which published on Jan. 4, 2007 and is incorporated by reference herein, describes system 400 in further detail.

Figure 5:
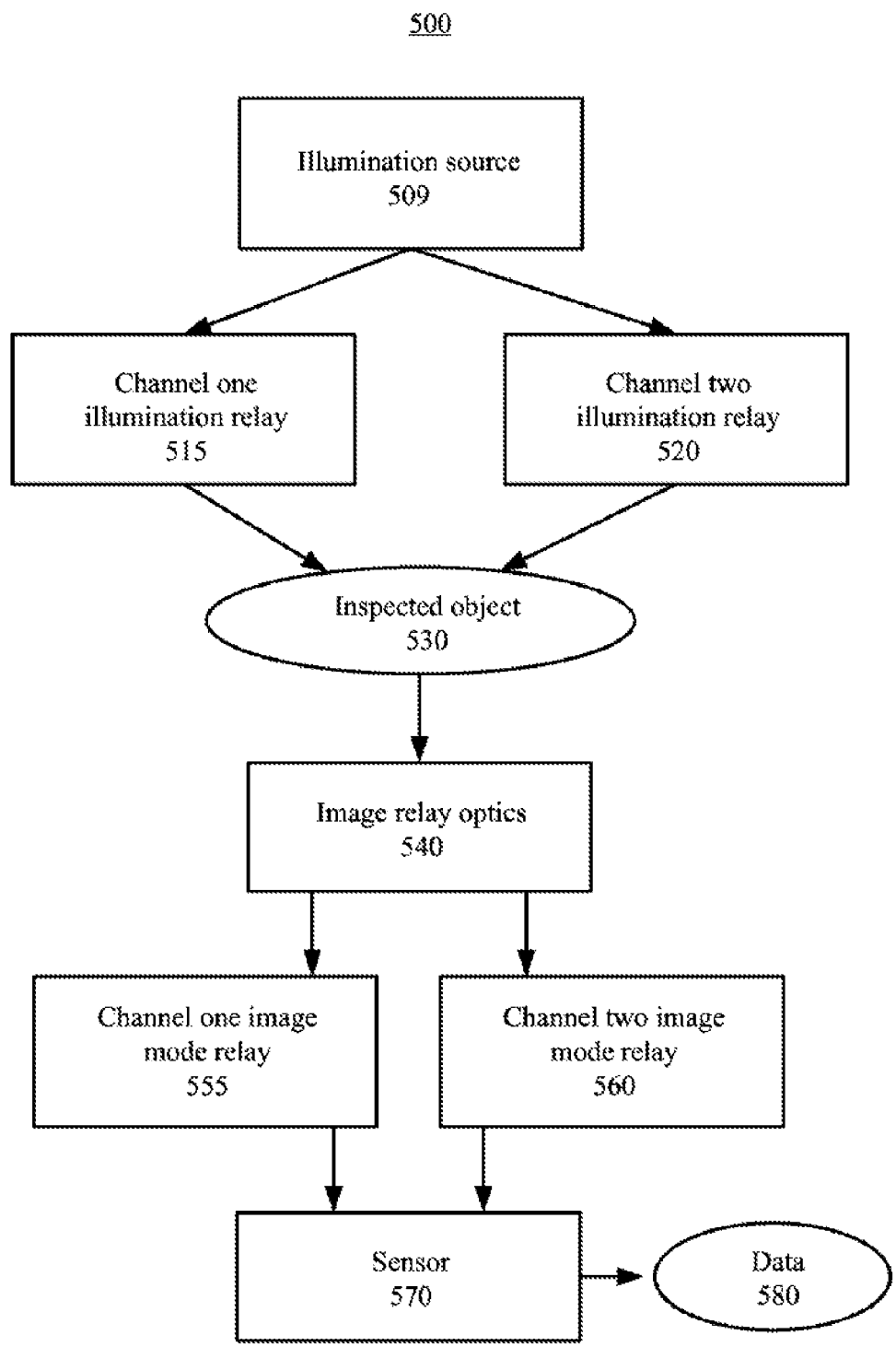
FIG. 5 illustrates an exemplary inspection system incorporating a split-readout backside illuminated avalanche image sensor.

FIG. 5 shows a reticle, photomask or wafer inspection system 500 that simultaneously detects two channels of image or signal on one backside illuminated avalanche image sensor 570. Backside illuminated avalanche image sensor 570 comprises a split-readout image sensor. Illumination source 509 incorporates a DUV laser. The operating wavelength of the DUV laser may be shorter than about 200 nm, such as a wavelength of approximately 193 nm. The two channels may comprise reflected and transmitted intensity when an inspected object 530 is transparent (for example a reticle or photomask), or may comprise two different illumination modes, such as angles of incidence, polarization states, wavelength ranges or some combination thereof. The light is directed to inspected object 530 using channel one illumination relay 515 and channel two illumination relay 520.

The inspected object 530 may be a reticle, a photomask, a semiconductor wafer or other article to be inspected. Image relay optics 540 can direct the light that is reflected and/or transmitted by inspected object 530 to a channel one image mode relay 555 and to a channel two image mode relay 560. Channel one image mode relay 555 is tuned to detect the reflection or transmission corresponding to channel one illumination relay 515, whereas channel two image mode relay sensor 560 is tuned to detect the reflection or transmission corresponding to channel two illumination relay 520. Channel one image mode relay 555 and channel two image mode relay sensor 560 in turn direct their outputs to backside illuminated avalanche sensor 570. The data corresponding to the detected signals or images for the two channels is shown as data 590 and is transmitted to a computer (not shown) for processing.

Other details of reticle and photomask inspection systems and methods that may be configured to measure transmitted and reflected light from a reticle or photomask are described in U.S. Pat. No. 7,352,457, which issued to Kvamme et al. on Apr. 1, 2008, and in U.S. Pat. No. 5,563,702, which issued to Emery et al. on Oct. 8, 1996, both of which are incorporated by reference herein.

Additional details regarding exemplary embodiments of image sensor 570 are provided in U.S. patent application Ser. No. 14/096,911, entitled "METHOD AND APPARATUS FOR HIGH SPEED ACQUISITION OF MOVING IMAGES USING PULSED ILLUMINATION", filed by Brown et al. on Dec. 4, 2013, and in U.S. Pat. No. 7,528,943 entitled "METHOD AND APPARATUS FOR SIMULTANEOUS HIGH-SPEED ACQUISITION OF MULTIPLE IMAGES" by Brown et al., which issued on May 5, 2009. These patents and patent applications are incorporated by reference herein.

Figure 6:
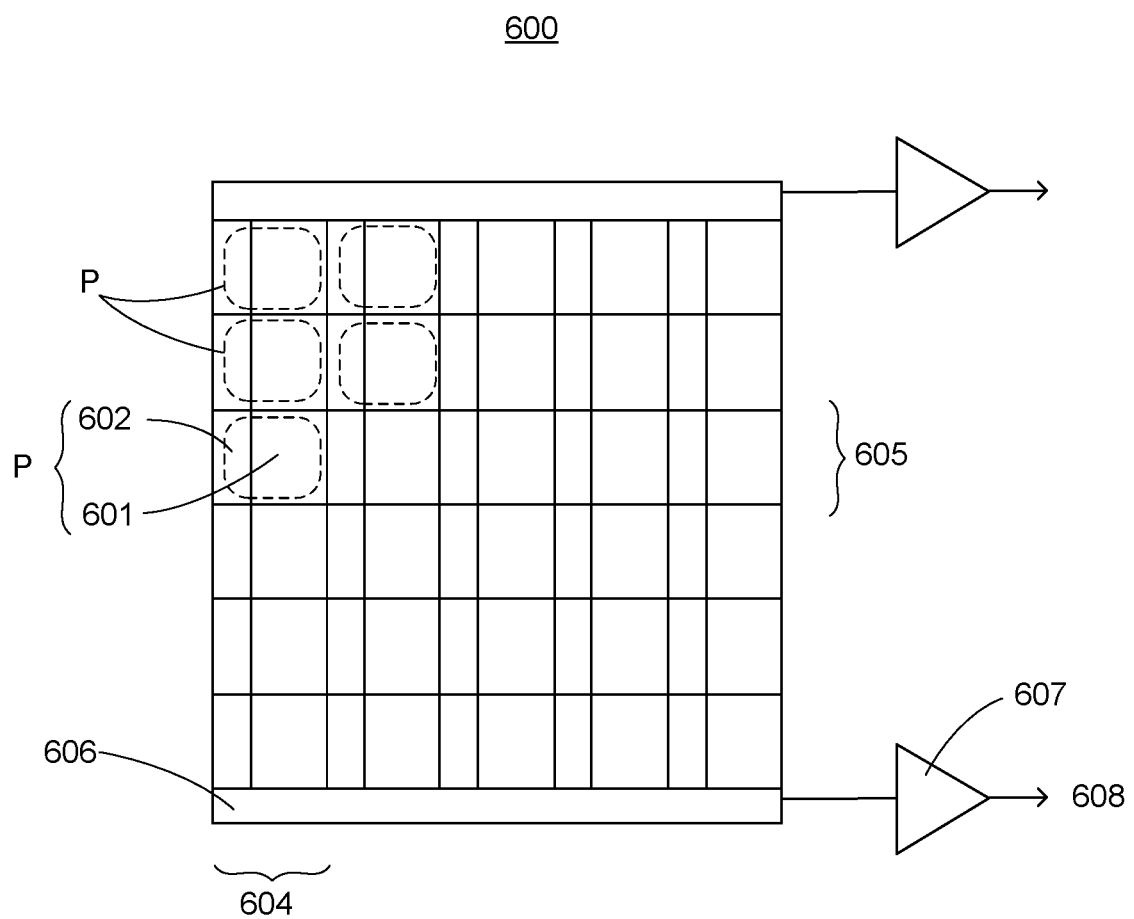
FIG. 6 illustrates an exemplary layout of a two-dimensional (2D) CMOS image sensor incorporating backside-illuminated avalanche sensing.
Figure 9:
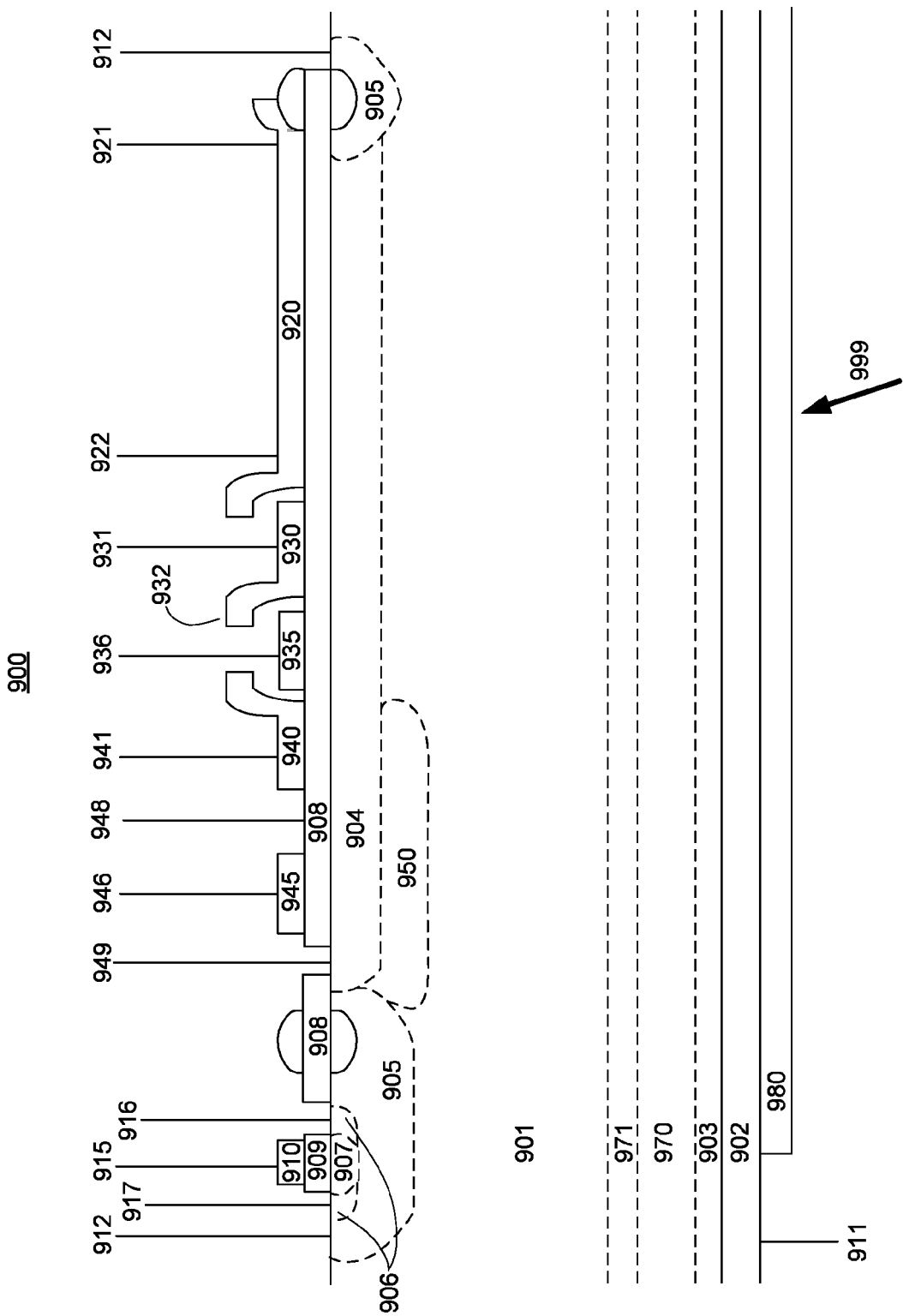
FIG. 9 illustrates key aspects of the design and fabrication of back-side illuminated avalanche image and line sensors.

FIG. 6 shows an exemplary layout of a 2D backside-illuminated avalanche image sensor 600 based on CMOS imaging technology. The image sensor comprises a 2D array of pixels P which, in turn, comprise a light signal collecting area 601 and associated pixel circuits 602. The pixels are laid out in columns such as 604 and rows such as 605. Key features of a pixel are illustrated in FIG. 9, which is described below. A row select signal (not shown) directs all the pixels of one row to output their signals. Column selector 606 can select one column and direct its signal to an output such as 608, via a buffer, amplifier or analog-to-digital converter 607. Image sensor 600 may output its signal in analog or digital format. Typically image sensor 600 has multiple outputs in order to be able to output image data at a total data rate of billions of pixels per second.

Figure 7:
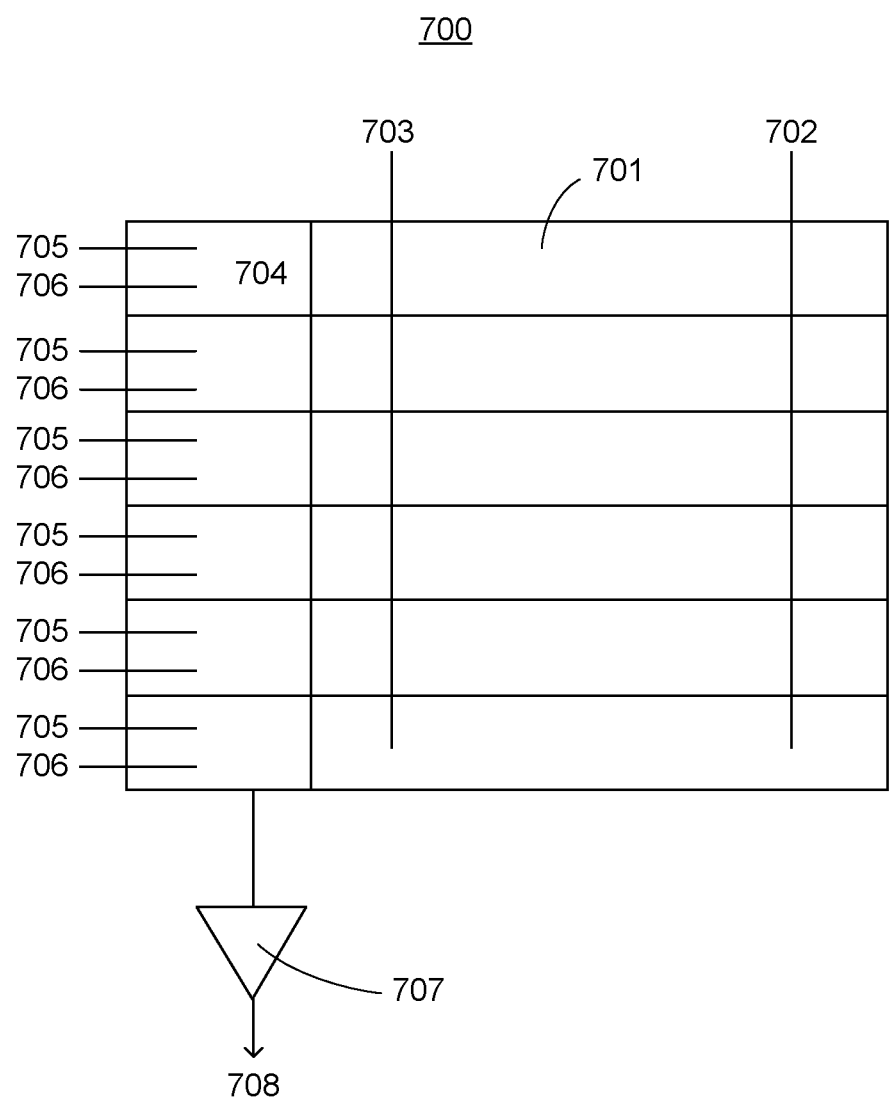
FIG. 7 illustrates an exemplary layout of a line sensor incorporating backside-illuminated avalanche sensing.

FIG. 7 shows an exemplary layout of a backside-illuminated avalanche line sensor 700. Multiple pixels such as 701 are laid out in one line. Two or more control voltages 702 and 703 are connected to the pixels to control where the electrons accumulate within the pixel as explained below in the description of FIG. 9. In one embodiment each pixel connects to a readout register 704. The readout registers are arranged in a line. Horizontal clocks 705 and 706 control the transfer of electrons from one horizontal register to the next so as to allow the signal to be sent to 707 which comprises a charge-to-voltage converter, a buffer and, optionally, an amplifier to drive output 708. In preferred embodiments (not shown), the readout registers are divided into multiple segments so that multiple outputs are used with between about 4 and about 128 pixels connect to one output. In another embodiment there is one output for every two pixels and no readout register transfer is needed. In another embodiment, charge-to-voltage conversion, buffering and, optionally, amplification, is done at each pixel and the output registers are replaced by a series of switches to allow each pixel to be connected to the output in turn. In such an embodiment multiple outputs are preferred with between 2 and 128 pixels per output.

Figure 8:
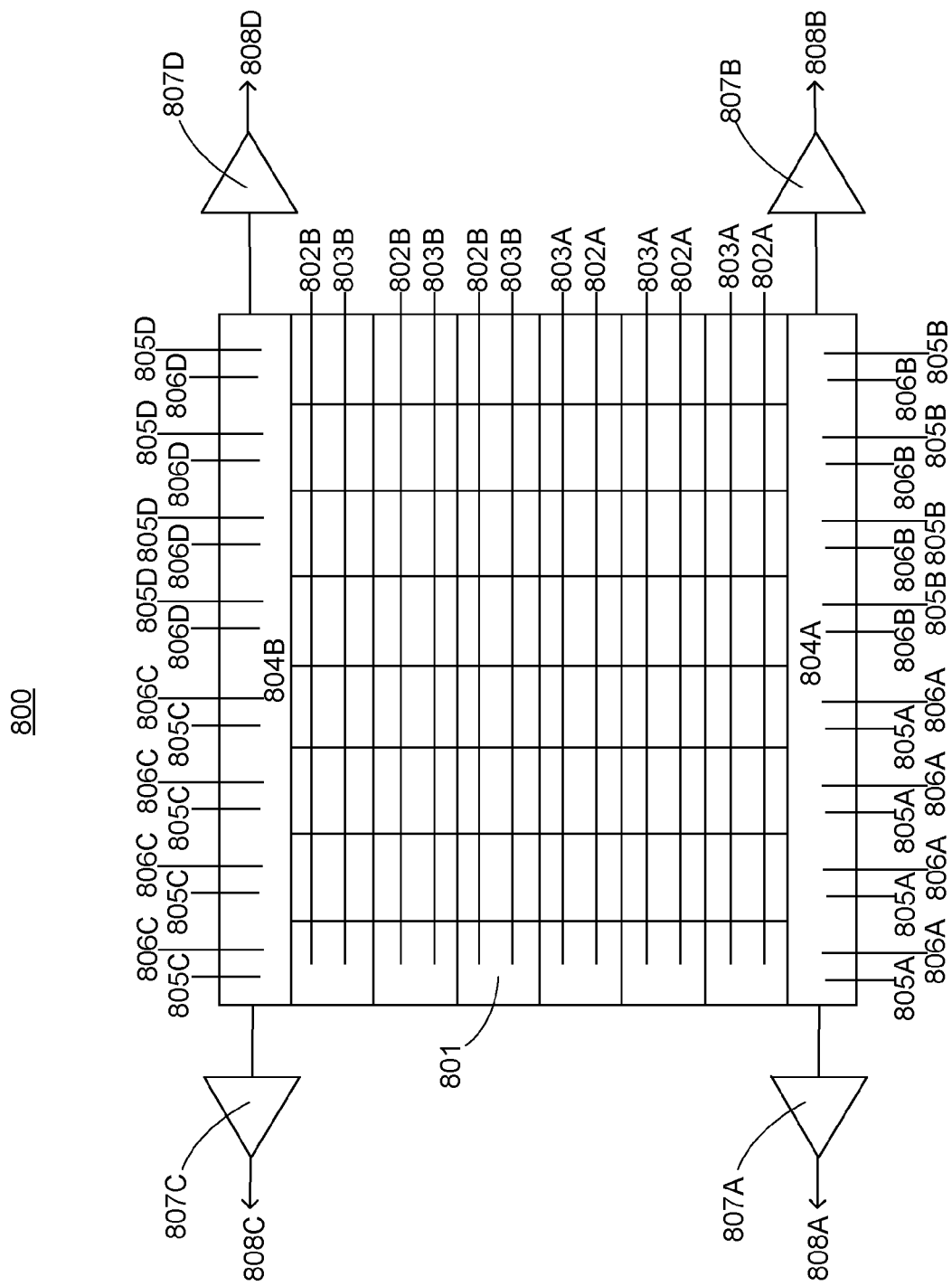
FIG. 8 illustrates an exemplary layout of a 2D CCD image sensor incorporating backside-illuminated avalanche sensing.

FIG. 8 shows an exemplary layout of a 2D backside-illuminated avalanche image sensor 800 based on CCD imaging technology. Multiple pixels such as 801 are arranged in columns and rows. Vertical clocks such as 802A, 803A, 802B and 803B cause the accumulated electrons in the image to transfer from one pixel to the next in the same column and eventually to horizontal register 804A or horizontal register 804B. Horizontal clocks 805A, 806A, 805B, 806B, 805C, 806C, 805D and 806D control the transfer of electrons within the horizontal registers to outputs 808A, 808B, 808C and 808D via 807A, 807B, 807C and 807D which each comprise a charge-to-voltage converter, a buffer and, optionally, an amplifier. Although the horizontal and vertical clocks are shown as two-phase clocks, this is merely for illustrative purposes and does not limit how the invention may be used. Two, three or four phase clocks may be used for the horizontal and vertical clocks. The horizontal and vertical clocks need not have the same number of phases. In some embodiments the horizontal register is only on one side of the pixel array (such as horizontal register 804A. Although each horizontal register is shown as divided in two, with each half transferring in opposite directions, the horizontal register may be a single register or, in preferred embodiments, may be divided into multiple segments which may all transfer in the same direction as one another. Hence the number of outputs may be greater than, or less than, the four shown. In one embodiment, there may be one output for every two columns.

The layout of part of one column of sensor 800 and other aspects of this sensor are further illustrated in FIG. 10 and described below in the descriptions of FIGS. 9 and 10.

FIG. 9 illustrates aspects of the design, fabrication and operation of a backside-illuminated avalanche sensor 900. Such a sensor may be fabricated with CMOS or CCD technology, or a combination thereof. Bipolar transistors (not shown) may be used in some of the circuits in combination with MOS transistors.

The sensor is fabricated in an intrinsic or lightly p-type doped (doping concentration less than or about $2 \times 10^{13}$ cm$^{-3}$) epitaxial layer 901 with a thickness that is between about 20 µm and about 200 µm (depending on the avalanche gain required, as well as other considerations such as the mechanical strength of the membrane after thinning the sensor). An n-type layer 904 (with, for example, a doping concentration of about $10^{16}$ cm$^{-3}$) is formed just under the top (front-side) surface of the epitaxial layer. Layer 904, when the sensor is properly biased forms a buried channel that is used to collect and transfer electrons. At either end of the n-type layer 904 is a p+ type layer 905 which has about 2× or higher doping concentration than the n-type layer. The p+ type layer 905 is grounded by electrical contacts such as 912. Layer 905 may be grounded in multiple locations.

A dielectric layer 908 is grown on the front surface of the epitaxial layer. Dielectric layer may comprise a single dielectric material, such as silicon dioxide, or it may comprise multiple layers of dielectric materials such as a silicon nitride layer on top of a silicon dioxide layer, or a three-layer stack such as silicon dioxide on silicon nitride on silicon dioxide. Typically dielectric layer thicknesses are in the range of about 50 nm to about 200 nm. Dielectric layer 908 has openings etched into it as appropriate to allow electrical contact to the underlying silicon where needed.

Multiple gate electrodes such as 920, 930, 935, 940 and 945 are deposited and patterned on top of dielectric layer 908. The gate electrodes are typically made of polysilicon or aluminum, but other conductive materials including other metals and semi-metallic compounds (such as TiN) may be used. Electrical connections such as 921, 922, 931, 936, 941 and 946 may be made to the gate electrodes.

In preferred embodiments, the gate electrodes overlap one another, as shown, for example at 932 in order to minimize and control fringe electric fields near the edges of the electrodes. The gate electrodes are separated by a dielectric material (not shown).

Circuits for amplifying or processing the signals and controlling the sensor may be fabricated inside the light sensitive area or adjacent to the light sensitive area. Such a circuit is illustrated by the MOSFET transistor formed by source/drain implants 906 (the source and drain are shown as having the same implants, but in some implementations the source and drain may be implanted differently), channel implant 906, gate dielectric 909 and gate electrode 910. Electrical connections may be made to this transistor, such as those shown as 916, 917 and 915. Typically such circuits comprise many transistors. One transistor is shown in FIG. 9 to illustrate key aspects of the inventive sensor without making the figure too complicated. An important aspect of the image sensors described herein is that MOSFET transistors with a n-type channel are fabricated in a p+ doped well 905 in order to electrically isolate them from dark currents and photocurrents in the epitaxial material 901, as well as to shield the transistor from the backside voltage 911 (which is described below). Note that the gate dielectric 909 may be substantially similar to dielectric layer 908 and may be formed at the same time, or dielectric layer 909 may be formed of different materials and/or different thicknesses than dielectric layer 908 as necessary to get the desired transistor characteristics. Although a single MOSFET transistor is illustrated in FIG. 9, NMOS, PMOS and bipolar transistors may be used as appropriate and may be electrically isolated by appropriate implanted layers such as 905 when necessary.

The back-side (light-sensitive) surface of epitaxial layer 901 is where light 999 is incident. A layer of pure boron 902 is deposited on the backside of epitaxial layer 901. In preferred embodiments, boron layer 902 is between about 3 nm and 6 nm thick. Boron layers much thinner than about 3 nm may have pinholes that allow the silicon underneath to oxidize. Under prolonged exposure to DUV or VUV light, charges and traps accumulate in silicon dioxide. These charges and traps degrade the performance of the sensor. Boron layers thicker than about 6 nm are typically not preferred because boron absorbs UV, DUV and VUV light, so the sensitivity of the sensor would be reduced by a thick boron layer. Methods of depositing a pure boron layer on silicon are described in the '166 US Patent Application cited above and in references cited in the '166 patent application.

A very highly doped p+ layer 903 is formed at the backside surface of the epitaxial layer by incidental or deliberate drive-in of the boron during the deposition of pure boron layer 902. In some embodiments, after depositing boron 902 on the backside of the epitaxial layer 901, the wafer is held at an elevated temperature (such as between about 800° C. and about 950° C.) for between about one and five minutes in order to drive in some boron. Controlling the temperature and time allows the boron profile to be tailored.

Adjacent to layer 903 near the backside surface of the epitaxial layer is an n-type doped layer 970. In a preferred embodiment, the thickness of n-type doped layer 970 is about 2 μm (such as a thickness between about 1 μm and 5 μm) and the concentration of the n-type dopant is about $2 \times 10^{16}$ cm$^{-3}$ (such as a dopant concentration of between about $5 \times 10^{15}$ cm$^{-3}$ and about $10^{17}$ cm$^{-3}$). Adjacent to n-type doped layer 970 is a thin highly doped p-type layer 971. In a preferred embodiment, the dopant concentration in thin highly doped p-type layer 971 is about $2 \times 10^{19}$ cm$^{-3}$ (such as a dopant concentration between about $5 \times 10^{18}$ cm$^{-3}$ and about $5 \times 10^{19}$ cm$^{-3}$), and the thickness of thin highly doped p-type layer 971 is about 25 nm (such as a thickness between about 10 nm and about 50 nm). Other combinations of dopant concentration and thickness are possible. The total number of active p dopants in thin highly doped p-type layer 971 should exceed the total number of active dopants in n-type doped layer 970, so that layer 970 is fully depleted. For example, if the dopant concentration in thin highly doped p-type layer 971 is much higher than $2 \times 10^{19}$ cm$^{-3}$, layer 971 may be thinner than 25 nm.

An electrical connection 911 is made to the boron layer so that the backside of the sensor may be biased to a negative voltage between about −10V and about −400V in order to make the sensor operate as an avalanche sensor.

In a preferred embodiment, one or more antireflection layers 980 is deposited on the boron layer in order to reduce the reflectivity of the sensor at wavelengths of interest and so improve the sensitivity of the sensor at those wavelengths.

When light 999 is absorbed in the silicon electron hole pairs are created. Hole moves to the backside surface where they recombine, whereas electrons are accelerated towards the n type layer 904 by the bias voltage applied to backside by contact 911. Because n-type doped layer 970 is fully depleted by thin highly doped p-type layer 971, most of the bias voltage appears across layer 970, resulting in a strong electric field within that layer. That strong electric field ensures that most electrons will gain enough energy to create additional electron hole pairs by collision as they travel through n-type doped layer 970. In one exemplary embodiment with an applied bias voltage of about 50V (such as a bias voltage between about 10V and about 100V), many electrons (such as between about 10 to about 50) may be generated per absorbed incident photon from light 999. When an electron gain of less than about 10 is required, a thinner n-type doped layer 970 (such as one about 1 μm thick) may suffice, and/or a lower bias voltage may be used. The amplification of the number of electrons allows the signal to be increased relative to the intrinsic noise of the sensor. CMOS technology, which may be unsuitable for high-speed image inspection because of its non-Poisson noise statistics can be made suitable for image inspection by avalanche amplification that reduces the non-Poisson component of the noise relative to the increased signal level. With high enough gain, such as a gain of about 20 to 30, single photons may be detectable above the noise level of a CMOS or CCD sensor.

Gate 920 may have two or more electrical connections such as those shown as 921 and 922. In such embodiments gate 920 comprises a resistive material such as intrinsic or lightly doped polysilicon so that a potential difference is created between the two or more electrical contacts. This potential difference is used to control where the collected electrons accumulate in n-type layer 904. Electrons will accumulate under a local maximum of the voltage in the gate 920. For example if contact 921 is at a voltage of −5V and contact 922 is at a voltage of −1V, electrons will accumulate under 922. By using multiple contacts on gate 920, non-monotonic voltage profiles may be created to accumulate electrons at a location that is under a location away from either end of 920. When a small pixel (such as less than about 10 μm is used), a single potential on gate 920 may be used to cause electrons to accumulate in n-type layer 904 under gate 920.

By raising the voltage on gate 930 applied by contact 931, electrons accumulated near that gate will move underneath that gate. A higher voltage (such as 10V to 15V) can be used to move the electrons faster when high-speed operation is required. When the pixel is small (such as smaller than about 10 μm) and the desired speed of operation is not too high, the voltage on gate 930 may suffice to empty the charge from the pixel fast enough without the assistance of a voltage gradient on electrode 920. In preferred embodiments, a voltage gradient on electrode 920 as described above ensures that the electrons transfer quickly under gate 930.

A more positive voltage than that applied to gate 930 (such as a few Volts more positive) is applied to gate 935 by contact 936. This causes the electrons to move rapidly under gate 936. The electrons can move in a few tens of nanoseconds. Lowering gate 930 to a voltage less than that applied by electrode 922 to gate 920 stops the transfer of electrons to the region under gate 935 and allows accumulation of the next image pixel under gate 920.

In one embodiment, such as sensor 700 illustrated in FIG. 7, a horizontal readout register comprises a series of gates similar to 940 arranged in a line perpendicular to the plane of FIG. 9. The electrons can be transferred from one gate to another by sequencing the voltages applied to the gates appropriately as is commonly used in CCDs. More, or fewer, gates may be used as required by the application. At the end of the horizontal register is a floating diffusion such as that shown under contact 948 for charge-to-voltage conversion. In sensor 700, the floating diffusion may not be located immediately adjacent to the light collecting pixel. It is so depicted in FIG. 9 merely for convenience. The operation of the floating diffusion is described below.

In another embodiment, such as sensor 600 illustrated in FIG. 6, there may be no horizontal readout register (and gate 940 may be omitted) and the electrons may be transferred directly to a floating diffusion such as the area under contact 948. A reset transistor such as that controlled by gate electrode 945 and connected to reset voltage 949 may be used to reset the floating diffusion prior to transferring the electrons from the pixel. The floating diffusion converts the charge of the electrons to a voltage and is routinely used in CCD sensors and CMOS sensors and will not be described in more detail here. Since the floating diffusion and reset transistor are in the light sensitive area in this embodiment, if necessary, the reset transistor and floating diffusion may be isolated from photocurrent and dark current by extending the p+ doped region 905 underneath the reset transistor and floating diffusion (as shown at 950). The output voltage on 948 may be connected to a buffer or amplifier before being connected to a row or column select, device output or analog to digital converter.

In sensor 600, each light sensitive pixel may have its own floating diffusion. In sensor 700, multiple pixels may share a floating diffusion through a horizontal register. In either case, the principles of operation of the floating diffusion are substantially similar.

There is more than one sequence in which the sensor of FIG. 9 may be fabricated. In one preferred embodiment, the front side doped regions (such as 904, 905, 906 and 907), the dielectric layers (such as 908 and 909) and polysilicon gate electrodes (such as 920 and typically some of the other gate electrodes) are formed while epitaxial layer 901 is on the surface of a wafer. In preferred embodiments, metal layers are not formed at this stage in the process. Then all, or part, of the wafer is removed by polishing and/or etching to expose, at least, the backside surface of the epitaxial layer in the light sensitive region of the sensor. Since the surface of the epitaxial layer adjacent to the wafer has a higher defect concentration than the bulk of the epitaxial layer, it is advantageous to polish or etch away a few microns of the backside of the epitaxial layer in order to improve the efficiency of the sensor.

Once the light sensitive area of the backside of the epitaxial layer is exposed, thin highly doped p-type layer 971 may be grown on that exposed surface by growing an epitaxial silicon layer with in-situ p-type doping at a very high dopant concentration. Then n-type doped layer 970 may be grown on layer 971 with in-site n-type doping. Since some boron (p-type dopant) may diffuse while layer 970 is being grown, layer 971 may be grown a little thinner and with higher dopant concentration than the final desired thickness and dopant concentration. Boron layer 902 can be deposited on n-type doped layer 970 and any additional needed drive-in of the boron to create layer 903 can be done. If desired, anti-reflection layer(s) may be deposited at this stage in the process, or later.

After the high temperature backside processes have been completed, metal layers may be deposited and patterned on the front surface.

In an alternative embodiment, n-type doped layer 970 is first grown epitaxially on a substrate wafer with in-situ n-type doping, then thin highly doped p-type layer 971 is grown epitaxially on top of n-type doped layer 970. Then epitaxial layer 901 is grown epitaxially on top of highly doped p-type layer 971. The entire front-side processing including metal layers may then be completed on the top surface of epitaxial layer 901 before exposing the backside of n-type doped layer 970. Since it is important to minimize diffusion of the p-type dopant in high doped p-type layer 971 during subsequent processing steps, thermal processing should preferably be done using rapid thermal annealing rather than furnace processes. Pure boron layer 902 is then deposited on n-type doped layer 970. A boron deposition temperature of about 450° C. may be used in order not to damage metal patterns on the front side. A laser or spike annealing process may be used to make the boron more uniform and to drive in some boron to form doped layer 903.

Methods of fabricating a backside illuminated boron-coated image sensor are described in the '166 US Patent Application cited above. If the process of exposing the backside of the epitaxial layer does not remove all of the wafer, then that wafer must be intrinsic or very lightly doped (such as a doping concentration of less than about $2 \times 10^{13}$ cm$^{-3}$) or must be protected on its backside by a thick dielectric layer, in order that the wafer does not conduct under the reverse bias voltage applied to the backside of the epitaxial layer.

Figure 10:
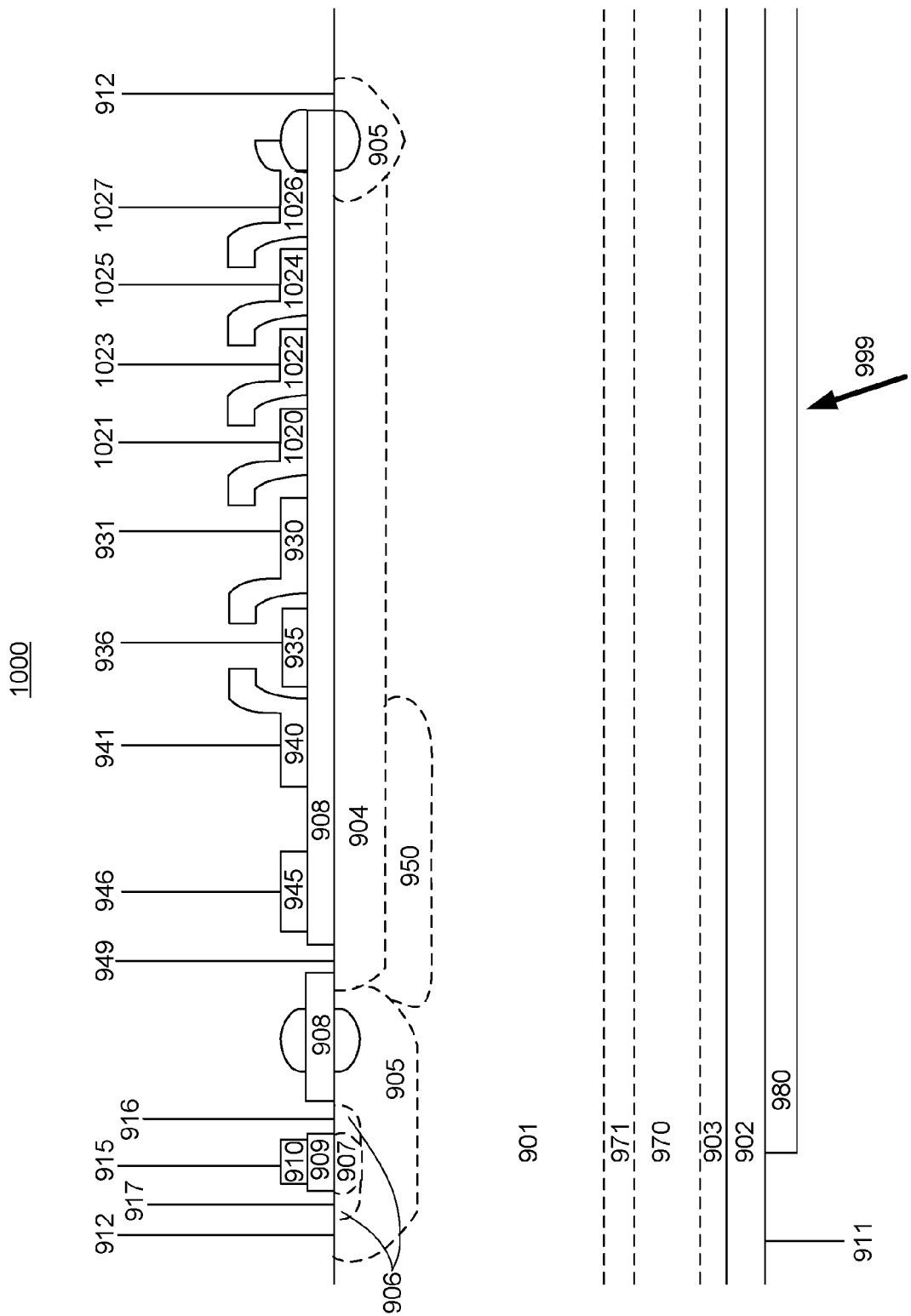
FIG. 10 illustrates key aspects of the design and fabrication of a back-side illuminated avalanche image sensor using CCD technology.

FIG. 10 illustrates aspects of the design, fabrication and operation of a backside-illuminated avalanche image sensor 1000 using CCD technology. Many features shown in FIG. 10 have substantially similar functions and are fabricated and operated in a substantially similar manner to the corresponding features of FIG. 9. Such features are labeled with the same label numbers as FIG. 9 and will not be described further here unless necessary to explain aspects specific to backside-illuminated avalanche image sensor 1000.

In image sensor 1000, a column of light sensitive pixels is formed under gates 1020, 1022, 1024 and 1026. Electrical connections 1021, 1023, 1025 and 1027 are respectively made to these gates. Although only four gates are shown to avoid making the figure too cluttered, in preferred embodiments many more gates would be used in order to form a large number of light collecting pixels (such as between about 4 and 4000 pixels). The gates are used to control the storage of charge and to transfer stored charge from one pixel to another. As is well known in CCD technology, the gates may be configured as a two phase, three phase or four phase clock (i.e. there are two, three or four gates per pixel respectively). A two-phase clock can only transfer charge in one direction, and has the advantage of simplifying the driving electronics if transfer is only required in one direction. Three and four phase clocks have the advantage of being able to transfer stored charges in either direction. As is well known, one of the gates in each pixel must be held a few volts more positive (such as about 5V to 15V more positive) than ground while the adjacent electrodes are held a few volts negative relative to ground (such as about −5V to −15V) to attract electrons from the epitaxial layer 901 to near (but not at) the surface of the n+ doped layer 904, where they will be stored until the gate voltages are changed to cause that stored charge to be transferred. In a TDI sensor the gates will be clocked at a rate that causes the charge to be transferred in synchrony with a moving image falling on the sensor (such as in synchrony the motion of the stage on which the specimen being inspected is held).

Typically multiple columns of pixels are laid out in a 2D array similar to that illustrated in FIG. 8. Vertical clocks connected across the whole array are used to transfer one pixel to the next within all, or a group of, columns simultaneously. One or more horizontal registers are used to transfer the signals from each column to one or more outputs.

Any of the above described backside-illuminated avalanche image sensors may use sine wave clocks or arbitrary waveform clocks to control the transfer of charge in horizontal and/or vertical directions as appropriate. The generation and use of such clock waveforms is described in more detail in U.S. Pat. No. 7,609,309 entitled "Continuous Clocking of TDI Sensors" to Brown et al., U.S. Pat. No. 7,952,633 entitled "Apparatus for Continuous Clocking of TDI Sensors" to Brown et al., and U.S. Utility patent application Ser. No. 14/273,424 entitled "LOW-NOISE SENSOR AND AN INSPECTION SYSTEM USING A LOW-NOISE SENSOR" and filed on May 8, 2014 by Brown et al. All of these patents and applications are incorporated by reference herein.

Further details of anti-reflection coatings that may be applied to the boron coating on the backside of the sensor can be found in U.S. patent application Ser. No. 12/476,190 entitled "Anti-Reflective Coating For Sensors Suitable For High Throughput Inspection Systems" and filed on Jun. 1, 2009 by Brown, and in U.S. patent application Ser. No. 14/591,325 entitled "Anti-reflection Layer for Back-Illuminated Sensor" and filed by Muramatsu et al. on Jan. 7, 2015. Both of these applications are incorporated by reference herein.

The various embodiments of the structures and methods of this invention that are described above are illustrative only of the principles of this invention and are not intended to limit the scope of the invention to the particular embodiments described. For example, the pixels of the sensors could be laid out in different configurations than those shown, and may comprise more or fewer pixels than shown, or the number of outputs could be larger or smaller than shown. In some embodiments only one or two outputs may be used. In preferred embodiments that are suited to use in high-speed inspection systems such as those used in the semiconductor industry (some of which are described herein), multiple outputs (such as several tens of outputs, a few hundred outputs, or one output per every two columns) are used to simultaneously output multiple pixels in order to achieve a high data output rate. Such sensors may comprise a linear array of about 1000 or a few thousand pixels, or may comprise a 2D array of about 1000 or a few thousand columns and between a few hundred and a few thousand pixels long.

The invention claimed is:

1. A method of fabricating a backside-illuminated avalanche image sensor, the method comprising:
    forming an intrinsic or p-doped silicon epitaxial layer on a silicon wafer with a p-dopant concentration less than $2 \times 10^{13}$ atoms per cubic centimeter ($cm^{-3}$);
    forming at least one of CMOS, CCD and bipolar circuits on a front-side surface of the epitaxial layer, said circuits comprising at least a buried n-type channel, and at least part of those circuits are formed in a p+-doped well with a doping concentration greater than $10^{16}$ atoms $cm^{-3}$;
    polishing or etching away the silicon wafer to expose a back-side surface of the epitaxial layer in at least a light sensitive area;
    epitaxially growing a p-type layer on the exposed surface with a dopant concentration greater than $5 \times 10^{18}$ dopant atoms $cm^{-3}$;
    epitaxially growing an n-type layer on the exposed surface with a dopant concentration between $5 \times 10^{15}$ dopant atoms $cm^{-3}$ and $10^{17}$ dopant atoms $cm^{-3}$; and
    depositing a pure boron coating on the exposed back-side surface of the epitaxial layer.

2. The method of claim 1, further comprising depositing an anti-reflection coating on the pure boron coating.

3. The method of claim 1, further comprising annealing the wafer for between 1 and 5 minutes at a temperature between 800° C. and 950° C. after depositing the pure boron coating.

4. The method of claim 1, wherein forming said intrinsic or p-doped silicon epitaxial layer comprises generating the epitaxial layer with a thickness between 20 μm and 200 μm.

5. A method of fabricating a backside-illuminated avalanche image sensor, the method comprising:
    epitaxially growing an n-type layer on a surface of a silicon wafer, the n-type layer having a dopant concentration between $5 \times 10^{15}$ dopant atoms $cm^{-3}$ and $10^{17}$ dopant atoms $cm^{-3}$ and a thickness between 1 μm and 5 μm;
    epitaxially growing a p-type layer on the surface of the n-type layer with a dopant concentration greater than $5 \times 10^{18}$ dopant atoms $cm^{-3}$ and a thickness between 10 nm and 50 nm;
    epitaxially growing an intrinsic or p-doped silicon epitaxial layer on the surface of the p-type layer with a p-dopant concentration less than $2 \times 10^{13}$ atoms $cm^{-3}$ and a thickness between 20 μm and 200 μm;
    forming at least one of CMOS, CCD and bipolar circuits on a front-side surface of the intrinsic or p-doped silicon epitaxial layer, said circuits comprising at least a buried n-type channel, and at least part of those circuits are formed in a p+-doped well with a doping concentration greater than $10^{16}$ atoms $cm^{-3}$;
    removing the silicon wafer to expose at least a part of a back-side surface of the n-type layer; and
    depositing a pure boron coating on the exposed back-side surface of the n-type layer.

6. The method of claim 5, further comprising depositing an anti-reflection coating on the pure boron coating.

7. A backside-illuminated avalanche sensor comprising:
    an epitaxial silicon layer;
    a thin highly doped p-type layer, an n-type doped layer and a boron layer disposed on a light-sensitive surface of the epitaxial silicon layer; and
    circuits formed on an opposing surface of the epitaxial silicon layer,
    wherein the epitaxial silicon layer comprises one of intrinsic silicon and p-type doped silicon with less than $2 \times 10^{13}$ dopant atoms $cm^{-3}$,
    wherein the circuits comprise an n-type doped buried channel and a resistive gate configured to control electron accumulation in the n-type doped buried channel,
    wherein at least some of the circuits are fabricated in a grounded p+ well with a dopant concentration greater than $10^{16}$ dopant atoms $cm^{-3}$,
    wherein the thin highly doped p-type layer comprises p-type doped silicon with a dopant concentration greater than $5 \times 10^{18}$ dopant atoms $cm^{-3}$, and a thickness of less than 50 nm, and
    wherein the n-type doped layer comprises n-type doped silicon with a dopant concentration between $5 \times 10^{15}$ dopant atoms $cm^{-3}$ and $10^{17}$ dopant atoms $cm^{-3}$, and a thickness of between 1 μm and 5 μm.

8. The sensor of claim 7,
    wherein the boron layer comprises pure boron having a thickness in the range of 2 nm to 6 nm, and
    wherein the sensor further comprises one or more anti-reflection layers disposed on the boron layer.

9. The sensor of claim 7, wherein the sensor further comprises means for maintaining the boron layer at a negative potential of between −10V and −400V relative to the opposing surface of the epitaxial layer.

10. The sensor of claim 7, wherein the circuits comprise at least one of CMOS image circuits, CCD circuits and bipolar transistors.

11. The sensor of claim 7, wherein the sensor comprises a linear array of pixels.

12. The sensor of claim 7, wherein the sensor comprises a two-dimensional array of pixels.

13. The sensor of claim 7, wherein each pixel comprises circuits including a floating diffusion region configured for charge-to-voltage conversion.

14. The sensor of claim 13, wherein the sensor further comprises one output for every two columns of pixels of the linear array.

* * * * *